(12) United States Patent
Crystal et al.

(10) Patent No.: US 10,293,059 B2
(45) Date of Patent: May 21, 2019

(54) GENE THERAPY TO PREVENT REACTIONS TO ALLERGENS

(71) Applicant: Cornell University, Ithaca, NY (US)

(72) Inventors: Ronald G. Crystal, New York, NY (US); Odelya E. Pagovich, New York, NY (US); Maria J. Chiuchiolo, Washington, DC (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 15/096,120

(22) Filed: Apr. 11, 2016

(65) Prior Publication Data

US 2016/0296638 A1   Oct. 13, 2016

Related U.S. Application Data

(60) Provisional application No. 62/145,035, filed on Apr. 9, 2015, provisional application No. 62/314,740, filed on Mar. 29, 2016.

(51) Int. Cl.
| | | |
|---|---|---|
| *A61K 48/00* | (2006.01) | |
| *A01K 67/027* | (2006.01) | |
| *C07K 16/42* | (2006.01) | |
| *C12N 15/85* | (2006.01) | |
| *C12N 15/86* | (2006.01) | |
| *A61K 39/395* | (2006.01) | |
| *A61K 49/00* | (2006.01) | |
| *C12N 7/00* | (2006.01) | |
| *A61K 39/00* | (2006.01) | |

(52) U.S. Cl.
CPC ...... *A61K 48/0066* (2013.01); *A01K 67/0271* (2013.01); *A01K 67/0278* (2013.01); *A61K 48/0091* (2013.01); *C07K 16/4291* (2013.01); *C12N 15/8509* (2013.01); *C12N 15/86* (2013.01); *A01K 2207/12* (2013.01); *A01K 2227/105* (2013.01); *A01K 2267/0387* (2013.01); *A61K 2039/505* (2013.01); *C07K 2317/24* (2013.01); *C07K 2317/76* (2013.01); *C12N 2015/8536* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 4,797,368 A | 1/1989 | Carter et al. | |
| 4,863,457 A | 9/1989 | Lee | |
| 5,378,475 A | 1/1995 | Smith et al. | |
| 5,443,505 A | 8/1995 | Wong et al. | |
| 5,464,758 A | 11/1995 | Gossen et al. | |
| 5,814,618 A | 9/1998 | Bujard et al. | |
| 6,342,390 B1 | 1/2002 | Wiener et al. | |
| 6,682,735 B2 | 1/2004 | Lowman et al. | |
| 6,723,551 B2 | 4/2004 | Kotin et al. | |
| 6,821,511 B2 | 11/2004 | Kotin et al. | |
| 7,112,715 B2 | 9/2006 | Chambon et al. | |
| 7,897,151 B2* | 3/2011 | Morsey | A61K 39/0008 424/144.1 |
| 8,236,527 B2* | 8/2012 | Chen | C07K 14/4716 435/320.1 |
| 2004/0229310 A1 | 11/2004 | Simmons | |
| 2009/0117124 A1* | 5/2009 | Liu | C07K 16/4291 424/141.1 |
| 2009/0202505 A1* | 8/2009 | Bartus | A61K 31/7088 424/93.21 |
| 2010/0113361 A1 | 5/2010 | Morsey et al. | |
| 2010/0136030 A1 | 6/2010 | Salah-Eddine et al. | |
| 2010/0143262 A1 | 6/2010 | Valenta et al. | |
| 2010/0189729 A1 | 7/2010 | Hoerr et al. | |
| 2011/0064726 A1 | 3/2011 | Liu et al. | |
| 2011/0065779 A1 | 3/2011 | Fang et al. | |
| 2012/0258107 A1 | 10/2012 | Graversen et al. | |
| 2013/0058936 A1 | 3/2013 | Bruenker et al. | |
| 2013/0236467 A1 | 9/2013 | Griggs et al. | |
| 2014/0336245 A1 | 11/2014 | Mingozzi et al. | |
| 2016/0123990 A1* | 5/2016 | High | C12N 15/86 435/5 |

FOREIGN PATENT DOCUMENTS

WO            99/01556 A2        1/1999

OTHER PUBLICATIONS

Aghaei et al., Bicistronic expression plasmid encoding allergen and anti-IgE single chain variable fragment antibody as a novel DNA vaccine for allergy therapy and prevention, Medical Hypotheses (2006) 67, 71-74.*
Kapturczak et al, Adeno-Associated Virus (AAV) as a Vehicle for Therapeutic Gene Delivery: Improvements in Vector Design and Viral Production Enhance Potential to Prolong Graft Survival in Pancreatic Islet Cell Transplantation for the Reversal of Type 1 Diabetes discloses, Current Molecular Medicine 2001, 1, 245-.*
Martin et al., CD4-mediated regulatory T-cell activation inhibits the development of disease in a humanized mouse model of allergic airway disease, J Allergy Clin Immunol 2012;129:521-8.*
Meijerink et al. , Immunomodulatory effects of potential probiotics in a mouse peanut sensitization model, FEMS Immunol Med Microbiol 65 (2012) 488-496.*
Gao et al., Novel adeno-associated viruses from rhesus monkeys as vectors for human gene therapy, PNAS, 11854-11859, Sep. 3, 2002, vol. 99, No. 18.*

(Continued)

*Primary Examiner* — Antonio Galisteo Gonzalez
(74) *Attorney, Agent, or Firm* — Leydig, Voit & Mayer, Ltd.

(57) ABSTRACT

This invention is directed to a vector which comprises a promoter operably linked to a nucleic acid sequence encoding a therapeutic gene that blocks allergic reactions. The invention is also directed to a composition comprising the vector and method of using the vector to reduce or inhibit an immune response or allergic reaction to an allergen in a mammal.

27 Claims, 19 Drawing Sheets

Specification includes a Sequence Listing.

(56) References Cited

OTHER PUBLICATIONS

Ganeshan et al., Impairing oral tolerance promotes allergy and anaphylaxis: A new murine food allergy model, J Allergy Clin Immunol 2009;123:231-8.*
Brehm et al., Humanized Mouse Models to Study Human Diseases, Curr Opin Endocrinol Diabetes Obes. Apr. 2010 ; 17(2): 120-125.*
Broekman et al., Adeno-Associated Virus Vectors Serotyped With Aav8 Capsid Are More Efficient Than Aav-1 or -2 Serotypes for Widespread Gene Delivery to The Neonatal Mouse Brain, Neuroscience 138 (2006) 501-510.*
Ausubel et al., Current Protocols in Molecular Biology, Greene Publishing Associates and John Wiley & Sons, NY, (1994) (Table of Contents only).
Bantel-Schaal et al., Human Adeno-Associated Virus Type 5 Is Only Distantly Related to Other Known Primate Helper-Dependent Parvoviruses, Journal of Virology, 73(2): 939-947 (1999).
Carter, Adeno-Associated Virus Vectors in Clinical Trials, Human Gene Therapy, 16: 541-550 (2005).
Cearley et al., Transduction Characteristics of Adeno-associated Virus Vectors Expressing Cap Serotypes 7, 8, 9, and Rh10 in the Mouse Brain, Molecular Therapy, 13(3): 528-537 (2006).
Chiorini et al., Cloning of Adeno-Associated Virus Type 4 (AAV4) and Generation of Recombinant AAV4 Particles, Journal of Virology, 71(9): 6823-6833 (1997).
Chiorini et al., Cloning and Characterization of Adeno-Associated Virus Type 5, Journal of Virology, 73(2): 1309-1319 (1999).
Daly et al., Neonatal gene transfer leads to widespread correction of pathology in a murine model of lysosomal storage disease, Proc. Natl. Acad. Sci. U.S.A., 96: 2296-2300 (1999).
De et al., High Levels of Persistent Expression of A1-Antitrypsin Mediated by the Nonhuman Primate Serotype rh.10 Adenoassociated Virus Despite Preexisting Immunity to Common Human Adeno-associated Viruses, Molecular Therapy, 13(1): 67-76 (2006).
Flotte, New AAV Serotypes May Broaden the Therapeutic Pipeline to Human Gene Therapy, Molecular Therapy, 13(1): 1-2 (2006).
Gao et al., Clades of Adeno-Associated Viruses Are Widely Disseminated in Human Tissues, Journal of Virology, 78(12): 6381-6388 (2004).
Gao et al., Novel adeno-associated viruses from rhesus monkeys as vectors for human gene therapy, Proc. Natl. Acad. Sci. USA, 99(18): 11854-11859 (2002).
Gao et al., Biology of AAV Serotype Vectors in Liver-Directed Gene Transfer to Nonhuman Primates, Molecular Therapy, 13(1): 77-87 (2006).
Goeddel, Systems for Heterologous Gene Expresssion, Gene Expression Technology: Methods in Enzymology, 185:3-7, Academic Press, San Diego, CA. (1990).
Harlow and Lane (eds.), Antibodies: A Laboratory Manual, CSH Press, Table of Contents only, pp. 1-19 (1988).
Holliger et al., Engineered antibody fragments and the rise of single domains, Nature Biotechnology, 23(9): 1126-1129 (2005).
Im et al., The AAV Origin Binding Protein Rep68 is an ATP-Dependent Site-Specific Endonuclease with DNA Helicase Activity, Cell, 61: 447-457 (1990).
Indra, et al., Temporarily-controlled site-specific mutagenesis in the basal layer of the epidermis: comparison of the recombinase activity of the tamoxifen-inducible Cre-ER$^T$ and Cre-ER$^{T2}$ recombinases, Nucleic Acids Research, 27(22): 4324-4327 (1999).
Janeway et al. (eds.), Immunobiology, 5th Ed., Garland Publishing, New York, NY, Table of Contents only, pp. 1-16 (2001).
Kramer et al., Transgene Control Engineering in Mammalian Cells , Methods in Molecular Biology, 308: 123-144 (2005).
Köhler et al., Derivation of specific antibody-producing tissue culture and tumor lines by cell fusion, European Journal of Immunology, 6: 511-519 (1976).
Lonberg, "Human antibodies from transgenic animals", Nature Biotechnology, 23(9): 1117-25 (2005).
Lonberg, "Human Monoclonal Antibodies from Transgenic Mice", Handb. Exp. Pharmacol., 181: 69-97 (2008).
Mao et al., Persistent Suppression of Ocular Neovascularization with Intravitreal Administration of AAVrh.10 Coding for Bevacizumab, Human Gene Therapy, 22: 1525-1535 (2011).
Niwa et al., Efficient selection for high-expression transfectants with a novel eukaryotic vector, Gene, 108: 193-200 (1991).
No et al., Ecdysone-inducible gene expression in mammalian cells and transgenic mice, Proc. Natl. Acad. Sci.USA, 93: 3346-3351 (1996).
Pereira et al., The Adeno-Associated Virus (AAV) Rep Protein Acts as both a Repressor and an Activator to Regulate AAV Transcription during a Productive Infection, Journal of Virology, 71(2): 1079-1088 (1997).
Remington, The Science and Practice of Pharmacy, 21st Edition, Lippincott Williams & Wilkins, Philadelphia, PA (2001) (Table of Contents only).
Rutledge et al., Infectious Clones and Vectors Derived from Adeno-Associated Virus (AAV) Serotypes Other Than AAV Type 2, Journal of Virology, 72(1): 309319 (1998).
Sambrook et al., Molecular Cloning: A Laboratory Manual, Fourth Edition, Cold Spring Harbor Press, Cold Spring Harbor, NY, (2001) (Table of Contents only).
Sondhi et al., Enhanced Survival of the LINCL Mouse Following CLN2 Gene Transfer Using the rh.10 Rhesus Macaque-derived Adeno-associated Virus Vector, Molecular Therapy, 15(3): 481-491 (2007).
Srivastava et al., Nucleotide Sequence and Organization of the Adeno-Associated Virus 2 Genome, Journal of Virology, 45(2): 555-564 (1983).
Watanabe et al., AAVrh.10-mediated genetic delivery of bevacizumab to the pleura to provide local anti-VEGF to suppress growth of metastatic lung tumors, Gene Therapy, 17(8): 1042-1051 (2010).
Wright et al., "Recombinant adeno-associated virus: Formulation challenges and strategies for a gene therapy vector", Current Opinion in Drug Discovery & Development, 6(2): 174-178 (2003).
Wright et al., "Identification of Factors that Contribute to Recombinant AAV2 Particle Aggregation and Methods to Prevent Its Occurrence during Vector Purification and Formulation", Molecular Therapy, 12(1): 171-178 (2005).
Wu et al., Adeno-associated Virus Serotypes: Vector Toolkit for Human Gene Therapy, Molecular Therapy, 14(3): 316-327 (2006).
Wu et al., Mutational Analysis of the Adeno-Associated Virus Type 2 (AAV2) Capsid Gene and Construction of AAV2 Vectors with Altered Tropism, Journal of Virology, 74(18): 8635-8647 (2000).
GenBank Accession Record No. U89790.1, submitted on Feb. 17, 1997.
GenBank Accession Record No. J01901.
GenBank Accession Record No. AF043303.1.
GenBank Accession Record No. AF085716.1.
WIPO, PCT International Search Report in Application No. PCT/US16/26977, dated Aug. 30, 2016, 5 pages.
Goldnau, "New strategies for the application of Adeno-Associated Virus type 2 targeting vectors," Disseitation to Obtain Doctoral Degree, Faculty of Chemistry and Pharmacy, Ludwig-Maximilians-University Munich (2006), obtained from https://pdfs.semanticscholar.org/967b/f18faac34ad7d134e8272e0254db5fc6e3af.pdf on Nov. 29, 2018.
Carton et al., "Codon engineering for improved antibody expression in mammalian cells", Protein Expression and Purification, 55: 279-286 (2007).
EBI Accession No. GS_PROT: AAW95648, Jun. 8, 1999.
EBI Accession No. GS_PROT: AAW95651, Jun. 8, 1999.
EBI Accession No. GS_PROT: AAW95658, Jun. 8, 1999.
European Patent Office, Partial Supplementary European Search Report in Application No. 16777501.4 (dated Jan. 16, 2019).

* cited by examiner

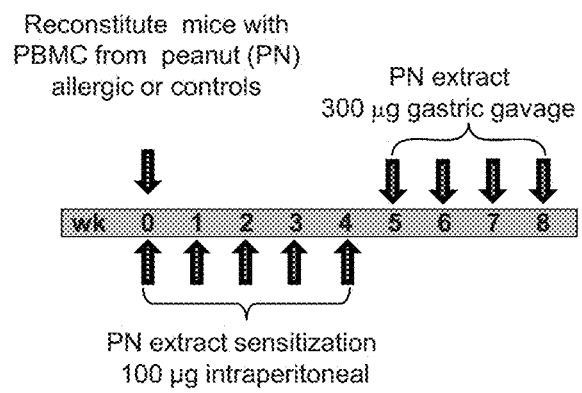
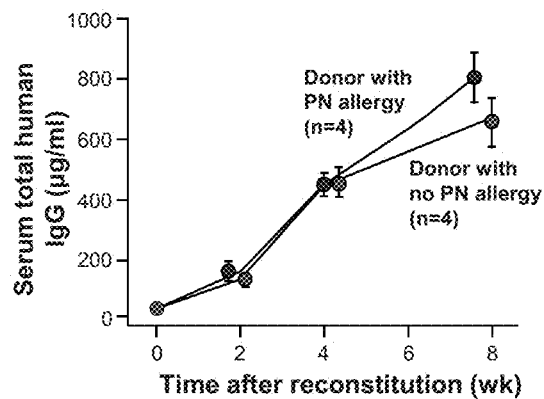

Post-PN challenge clinical phenotype

Donor with no PN allergy (wk 5)

Donor with PN allergy (wk 5)

Anaphylaxis score (wk 5)

$p=0.012$

Donor with no PN allergy (n=3)

Donor with PN allergy (n=3)

Passive cutaneous anaphylaxis (wk 7.5)

2 wk post-omalizumab 2 wk post-omalizumab

*In vitro* directed expression

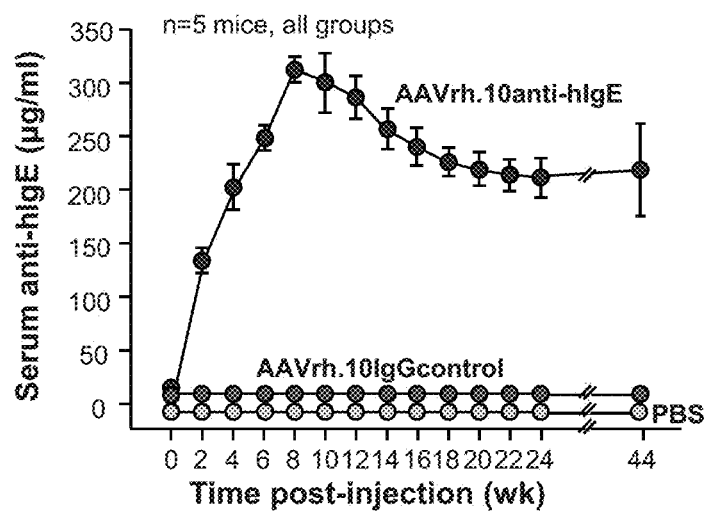

Prophylactic therapy before peanut (PN) sensitization

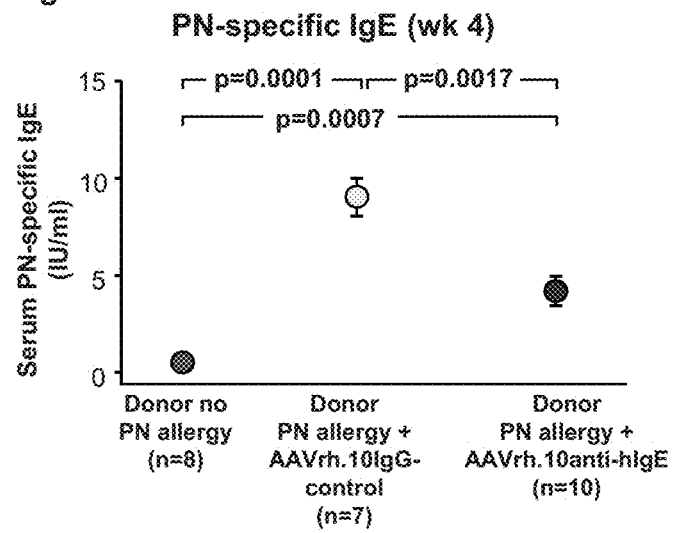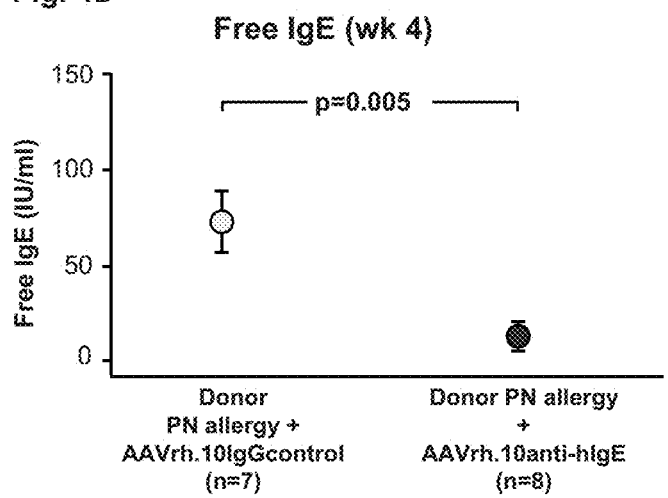

Post-peanut (PN) challenge phenotype (wk 6)

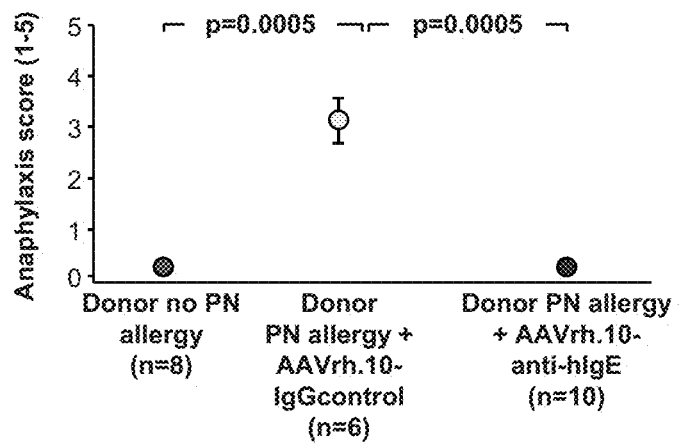
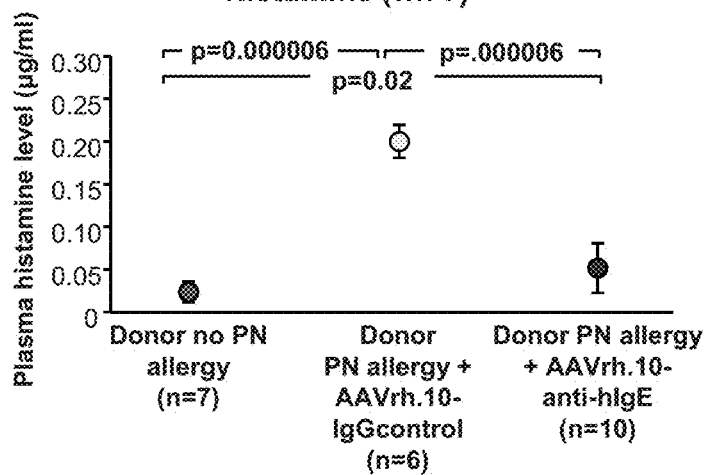

Passive cutaneous anaphylaxis (wk 7.5)

Treatment after peanut (PN) sensitization

Total human IgE

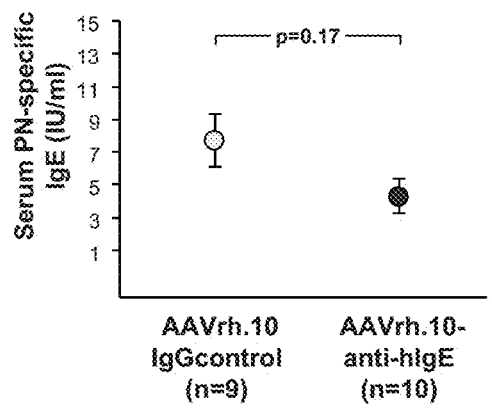
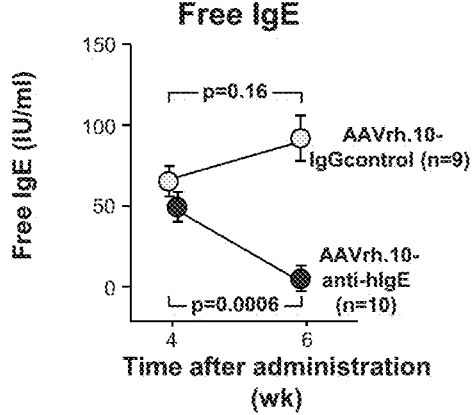

Post-peanut (PN) challenge clinical phenotype

Passive cutaneous anaphylaxis

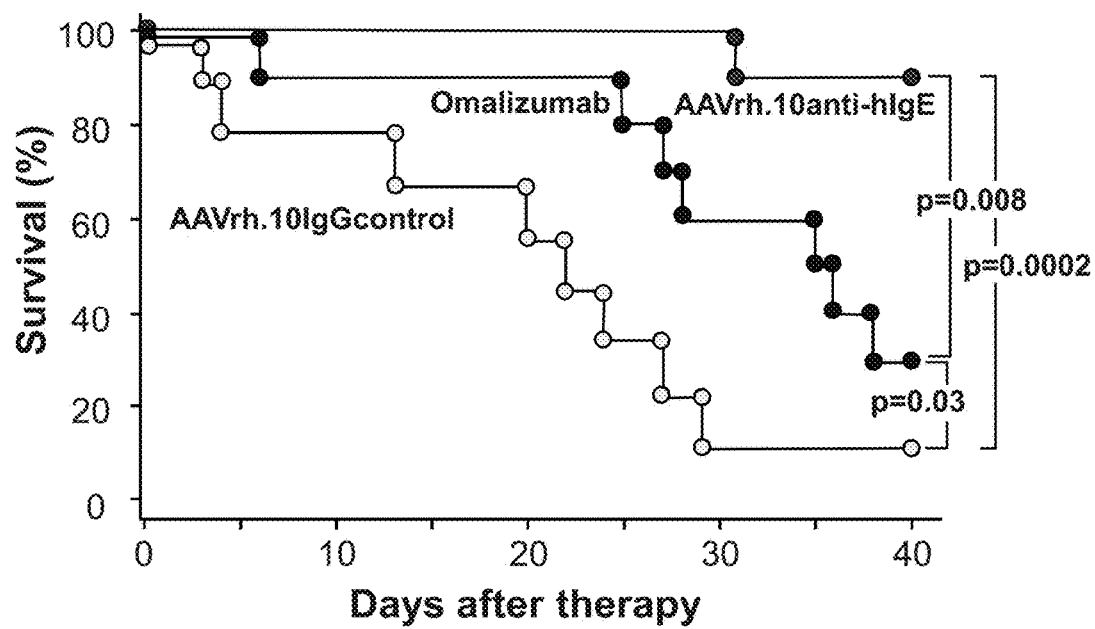

SEQUENCE LISTING

```
<160> NUMBER OF SEQ ID NOS: 11

<210> SEQ ID NO 1
<211> LENGTH: 36
<212> TYPE: DNA
<213> ORGANISM: Artificial Sequence
<220> FEATURE:
<223> OTHER INFORMATION: Synthetic Heavy Chain CDR-H3

<400> SEQUENCE: 1
cgccgtgagc ggctacagca tcaccagcgg ctacag                              36

<210> SEQ ID NO 2
<211> LENGTH: 30
<212> TYPE: DNA
<213> ORGANISM: Artificial Sequence
<220> FEATURE:
<223> OTHER INFORMATION: Synthetic Heavy Chain CDR-H2

<400> SEQUENCE: 2
cagcatcacc tacgacggca gcaccaacta                                     30

<210> SEQ ID NO 3
<211> LENGTH: 42
<212> TYPE: DNA
<213> ORGANISM: Artificial Sequence
<220> FEATURE:
<223> OTHER INFORMATION: Synthetic Heavy Chain CDR-H3

<400> SEQUENCE: 3 cgctcgggc agccactact tcggccactg gcacttcgcc gt                        42

<210> SEQ ID NO 4
<211> LENGTH: 45
<212> TYPE: DNA
<213> ORGANISM: Artificial Sequence
<220> FEATURE:
<223> OTHER INFORMATION: Synthetic Light Chain CDR-L1

<400> SEQUENCE: 4
ccgggctagc cagagcgtgg actacgacgg cgacagctac atgaa                    45

<210> SEQ ID NO 5
<211> LENGTH: 24
<212> TYPE: DNA
<213> ORGANISM: Artificial Sequence
```

```
<220> FEATURE:
<223> OTHER INFORMATION: Synthetic Light Chain CDR-L2

<400> SEQUENCE: 5
ctacgctgcc agctacctgg agag                                          24

<210> SEQ ID NO 6
<211> LENGTH: 27
<212> TYPE: DNA
<213> ORGANISM: Artificial Sequence
<220> FEATURE:
<223> OTHER INFORMATION: Synthetic Light Chain CDR-L3

<400> SEQUENCE: 6
ccagcagagc cacgaggacc cctacac                                       27

<210> SEQ ID NO 7
<211> LENGTH: 363
<212> TYPE: DNA
<213> ORGANISM: Artificial Sequence
<220> FEATURE:
<223> OTHER INFORMATION: Synthetic Heavy Chain Variable Region

<400> SEQUENCE: 7
gaggtgcagc tggtggagag cggcggtggc ctggtgcagc ctggtggtag cctgcgcctg    60
agctgcgccg tgagcggcta cagcatcacc agcggctaca gctggaactg gatccggcag   120
gcccctggca agggcctgga gtgggtggcc agcatcacct acgacggcag caccaactac   180
gccgacagcg tgaagggccg gttcaccatc agccgggacg acagcaagaa cacccttctac  240 ctgcagatga actccctgcg ggccgaggac accgccgtgt actactgcgc tcggggcagc   300
cactacttcg ccactggca cttcgccgtg tggggtcagg gcaccctggt gaccgtgagc    360
agc                                                                363

<210> SEQ ID NO 8
<211> LENGTH: 330
<212> TYPE: DNA
<213> ORGANISM: Artificial Sequence
<220> FEATURE:
<223> OTHER INFORMATION: Synthetic Light Chain Variable Region

<400> SEQUENCE: 8
gacatccagc tgacccagag ccctagcagc ctgagcgcca gcgtgggcga ccgggtgacc    60
atcacctgcc gggctagcca gagcgtggac tacgacggcg acagctacat gaattggtac   120
cagcagaagc ccggcaaggc tcccaagctg ctgatctacg ctgccagcta cctggagagc   180
ggcgtgccca gccggttcag cggcagcggc agcggcaccg acttcaccct gaccatcagc   240
agcctgcagc ccgaggactt cgccacctac tactgccagc agagccacga ggacccctac   300
accttcggcc agggcaccaa ggtggagatc                                   330

<210> SEQ ID NO 9
<211> LENGTH: 2214
<212> TYPE: DNA
<213> ORGANISM: Artificial Sequence
<220> FEATURE:
<223> OTHER INFORMATION: Synthetic Anti-IgE antibody

<400> SEQUENCE: 9
atggagttcg gcctgagctg gctgttcctg gtggccatcc tgaagggcgt gcagtgcgag    60
gtgcagctgg tggagagcgg cggtggcctg gtgcagcctg gtggtagcct gcgcctgagc   120
```

```
tgcgccgtga gcggctacag catcaccagc ggctacagct ggaactggat ccggcaggcc      180
cctggcaagg gcctggagtg ggtggccagc atcacctacg acggcagcac caactacgcc      240
gacagcgtga agggccggtt caccatcagc cgggacgaca gcaagaacac cttctacctg      300
cagatgaact ccctgcgggc cgaggacacc gccgtgtact actgcgctcg ggcagccac       360
tacttcggcc actggcactt cgccgtgtgg ggtcagggca cctggtgac cgtgagcagc       420
gccagcacca agggcccag cgtgttccct ctggctccct cttccaaatc caccagcggc       480
ggcaccgctg ccctgggctg cctggtgaag gactacttcc ccgagccgt gaccgtgagc       540
tggaacagcg gcgccctgac cagcggcgtg cacaccttcc ctgccgtgct gcaatccagc      600
ggcctgtaca gcctgagcag cgtcgtgacc gtgcccagca gcagcctggg cacccagacc      660
tacatctgca acgtgaacca caagcccagc aacaccaagg tggacaagaa ggccgagccc      720
aagagctgcg acaagaccca cacctgccct ccctgccccg ccctgagct gctcggcgga      780
cccagcgtgt tcctgttccc tcccaagccc aaggacaccc tgatgatcag ccggaccct      840
gaggtgacct gcgtggtcgt ggacgtgagc cacgaggacc ccgaggtgaa gttcaactgg      900
tatgtggacg gcgtggaggt gcacaacgcc aagaccaagc ccggggaga gcagtacaac      960
agcacctacc gggtggtgag cgtgctgacc gtgctgcacc aggactggct gaacggcaag     1020
gagtacaagt gcaaggtctc caacaaggcc ctgcctgccc ctatcgagaa gaccatcagc     1080
aaggccaagg gccagccccg ggagcccag gtgtacaccc tgcctcctag ccgggacgag     1140
ctgaccaaga accaggtctc cctgacctgc ctggtgaagg gcttctaccc cagcgacatc     1200
gccgtggagt gggagagcaa cggccagccc gagaacaact acaagaccac ccctcccgtg     1260
ctggacagcg acggcagctt cttcctgtac tccaagctga ccgtggacaa gagccggtgg     1320
cagcagggca acgtgttcag ctgcagcgtg atgcacgagg ccctgcacaa ccactacacc     1380
cagaagagc tgagcctgag ccccggacgg aagcggagga gcggcgctcc tgtgaagcag     1440
accctgaact tcgacctgct gaagctggcc ggcgacgtgg agagcaaccc tgggcctatg     1500
aagtacctgc tgcccaccgc cgctgctggc ctgctcctgc tcgctgccca acccgctgct     1560
gacatccagc tgacccagag ccctagcagc ctgagcgcca gcgtgggcga ccgggtgacc     1620
atcacctgcc gggctagcca gagcgtggac tacgacggcg acagctacat gaattggtac     1680
cagcagaagc ccggcaaggc tcccaagctg ctgatctacg ctgccagcta cctggagagc     1740
ggcgtgccca gccggttcag cggcagcggc agcggcaccg acttcaccct gaccatcagc     1800
agcctgcagc ccgaggactt cgccacctac tactgccagc agagccacga ggaccctac      1860
accttcggcc agggcaccaa ggtggagatc aagcggaccg tggccgctcc tagcgtgttc     1920
atcttccctc cctccgacga gcagctgaag agcggcaccg ccagcgtggt gtgcctgctg     1980
aacaacttct accctcggga ggccaaggtg cagtggaagg tggacaacgc cctgcagagc     2040
ggcaacagcc aggagagcgt gaccgagcag gacagcaagg acagcaccta cagcctgagc     2100
agcaccctga ccctgagcaa ggccgactac gagaagcaca aggtgtacgc ctgcgaggtg     2160
acccaccagg gcctgagcag ccccgtgacc aagagcttca ccggggcga gtgc            2214
```

<210> SEQ ID NO 10
<211> LENGTH: 1407
<212> TYPE: DNA
<213> ORGANISM: Artificial Sequence
<220> FEATURE:
<223> OTHER INFORMATION: Synthetic omalizumab heavy chain

```
<400> SEQUENCE: 10
atggagttcg gcctgagctg gctgttcctg gtggccatcc tgaagggcgt gcagtgcgag      60
gtgcagctgg tggagagcgg cggtggcctg gtgcagcctg gtggtagcct gcgcctgagc     120
tgcgccgtga gcggctacag catcaccagc ggctacagct ggaactggat ccggcaggcc     180
cctggcaagg gcctggagtg ggtggccagc atcacctacg acggcagcac caactacgcc     240
gacagcgtga agggccggtt caccatcagc cgggacgaca gcaagaacac cttctacctg     300
cagatgaact ccctgcgggc cgaggacacc gccgtgtact actgcgctcg gggcagccac     360
tacttcggcc actggcactt cgccgtgtgg ggtcagggca ccctggtgac cgtgagcagc     420
gccagcacca agggccccag cgtgttccct ctggctccct cttccaaatc caccagcggc     480
ggcaccgctg ccctgggctg cctggtgaag gactacttcc ccgagcccgt gaccgtgagc     540
tggaacagcg gcgccctgac cagcggcgtg cacaccttcc ctgccgtgct gcaatccagc     600
ggcctgtaca gcctgagcag cgtcgtgacc gtgcccagca gcagcctggg cacccagacc     660
tacatctgca acgtgaacca caagcccagc aacaccaagg tggacaagaa ggccgagccc     720
aagagctgcg acaagaccca cacctgcccc ccctgccccg ccctgagct gctcggcgga     780 cccagcgtgt tcctgttccc tcccaagccc aaggacaccc tgatgatcag ccggaccct     840 gaggtgacct gcgtggtcgt ggacgtgagc cacgaggacc ccgaggtgaa gttcaactgg     900
tatgtggacg gcgtggaggt gcacaacgcc aagaccaagc ccgggagga gcagtacaac     960 agcacctacc gggtggtgag cgtgctgacc gtgctgcacc aggactggct gaacggcaag    1020
gagtacaagt gcaaggtctc caacaaggcc ctgcctgccc ctatcgagaa gaccatcagc    1080
aaggccaagg gccagccccg ggagcccag gtgtacaccc tgcctcctag ccgggacgag    1140
ctgaccaaga accaggtctc cctgacctgc ctggtgaagg gcttctaccc cagcgacatc    1200
gccgtggagt gggagagcaa cggccagccc gagaacaact acaagaccac ccctcccgtg    1260
ctggacagcg acggcagctt cttcctgtac tccaagctga ccgtggacaa gagccggtgg    1320
cagcagggca acgtgttcag ctgcagcgtg atgcacgagg ccctgcacaa ccactacacc    1380
cagaagagcc tgagcctgag ccccgga                                        1407

<210> SEQ ID NO 11
<211> LENGTH: 645
<212> TYPE: DNA
<213> ORGANISM: Artificial Sequence
<220> FEATURE:
<223> OTHER INFORMATION: Synthetic omalizumab light chain

<400> SEQUENCE: 11
gacatccagc tgacccagag ccctagcagc ctgagcgcca gcgtgggcga ccgggtgacc      60
atcacctgcc gggctagcca gagcgtggac tacgacggcg acagctacat gaattggtac     120 cagcagaag ccggcaaggc tcccaagctg ctgatctacg ctgccagcta cctggagagc     180
ggcgtgccca gccggttcag cggcagcggc agcggcaccg acttcaccct gaccatcagc     240
agcctgcagc ccgaggactt cgccacctac tactgccagc agagccacga ggaccctac     300 accttcggcc agggcaccaa ggtggagatc aagcggaccg tggccgctcc tagcgtgttc     360
atcttccctc cctccgacga gcagctgaag agcggcaccg ccagcgtggt gtgcctgctg     420
aacaacttct accctcggga ggccaaggtg cagtggaagg tggacaacgc cctgcagagc     480
ggcaacagcc aggagagcgt gaccgagcag gacagcaagg acagcaccta cagcctgagc     540
```

```
agcaccctga ccctgagcaa ggccgactac gagaagcaca aggtgtacgc ctgcgaggtg    600
acccaccagg gcctgagcag ccccgtgacc aagagcttca ccgg                     645
```

GENE THERAPY TO PREVENT REACTIONS TO ALLERGENS

CROSS-REFERENCE TO RELATED APPLICATIONS

This patent application claims the benefit of U.S. Provisional Patent Application No. 62/314,740, filed Mar. 29, 2016, and U.S. Provisional Patent Application No. 62/145,035, filed Apr. 9, 2015, which are incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 8,749 Byte ASCII (Text) file named "723435_ST25.TXT," created on Apr. 11, 2016.

BACKGROUND OF THE INVENTION

Allergens evoke a variety of reactions in susceptible individuals, ranging from rash to fatal anaphylactic reactions. These reactions are mediated by type I hypersensitivity responses linked to allergen antigen-specific immunoglobulin E (IgE). There has been considerable interest in treating allergic individuals with therapies that interrupt allergen-specific IgE from eliciting anaphylaxis. One such approach is treatment with the recombinant DNA-derived humanized Ig1$_\kappa$ monoclonal antibody, omalizumab (Xolair®), which binds to human IgE. Omalizumab inhibits the binding of IgE to the IgE receptor on the surface of mast cells and basophils, thus limiting the degree of release of mediators of the allergic response.

The challenge in using an anti-IgE monoclonal antibody as a prophylactic treatment against allergen-induced anaphylaxis in sensitive individuals is that the protection provided by a single administration of omalizumab is estimated to be 2 to 4 weeks. The short half-life of current therapies requires at least monthly parenteral administration of omalizumab to maintain persistent effective therapy.

Therefore, there is a need to develop alternative compositions and methods to administer an IgE specific antibody and prophylactically treat allergen-induced anaphylaxis. This invention provides such compositions and methods. This and other advantages of the invention will become apparent from the detailed description provided herein.

BRIEF SUMMARY OF THE INVENTION

The invention provides a vector comprising a promoter operably linked to a nucleic acid sequence that encodes an anti-IgE antibody or antigen binding fragment thereof, or encodes a soluble IgE receptor, an eosinophil, a basophil, IL-13, or IL-4. The invention also provides a composition comprising the vector, and a method of using the vector to inhibit or reduce an immune response or allergic reaction to an allergen in a mammal. Additionally, the invention provides a method of providing a recombinant humanized mouse model of allergy.

BRIEF DESCRIPTION OF THE SEVERAL VIEWS OF THE DRAWING(S)

Figure 1C:
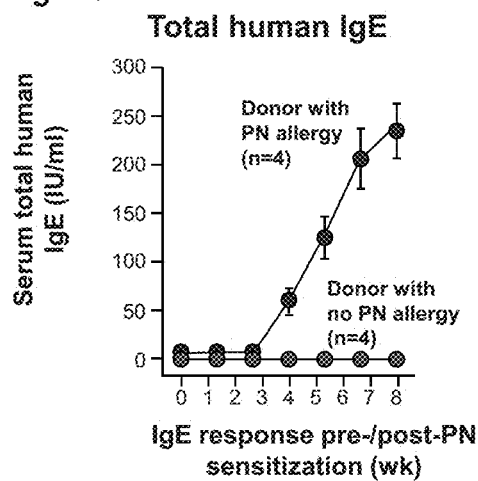
FIGS. 1B-1D are graphs which depict experimental data illustrating the levels of total human IgG (FIG. 1B), total human IgE (FIG. 1C) and peanut-specific IgE (FIG. 1D) in NOD-scid-IL2Rgamma$^{null}$ (NSG) mice reconstituted with human blood mononuclear cells from a peanut allergic or control donor, as measured by ELISA (mean±SEM, n=4/group).
Figure 1D:
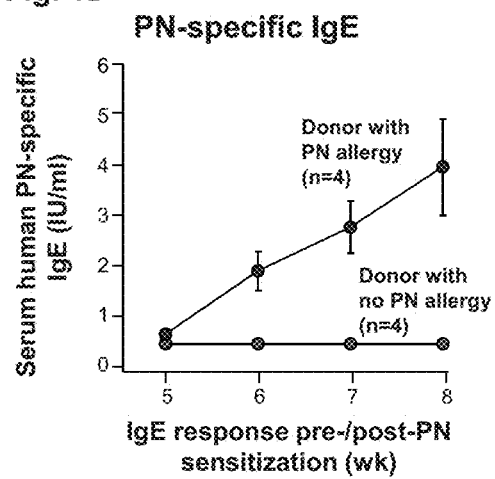
Figure 1E:
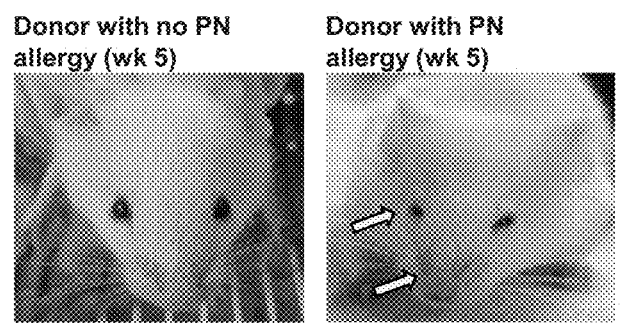
FIG. 1A is a schematic of the protocol for the development of a recombinant humanized mouse model for allergy.

FIG. 1E provides images of mice after peanut extract challenge. Left panel—mouse reconstituted with mononuclear cells from a non-allergic donor which appears normal after peanut challenge. Right panel—mouse reconstituted with mononuclear cells from a peanut allergic donor which displays puffiness around the eyes/snout, pilar erecti, and itching/ruffling of fur 1 minute after peanut challenge.

Figure 1F:
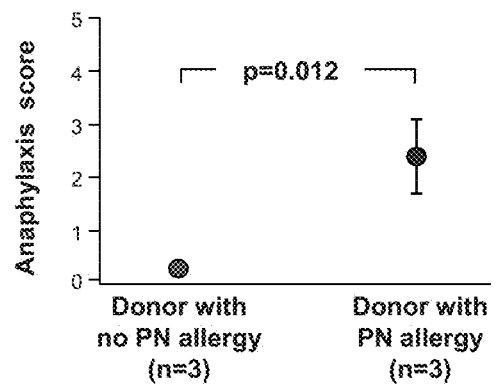
Figure 1G:
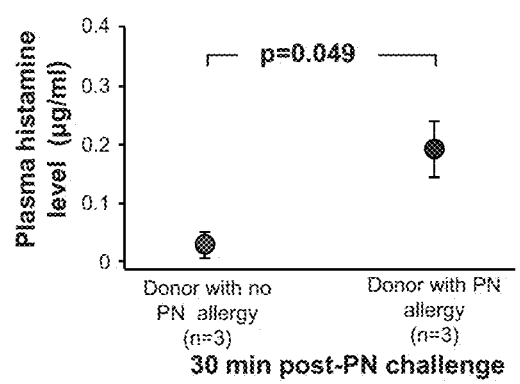

FIGS. 1F-1G are graphs of experimental data illustrating the anaphylaxis score (1 to 5) (FIG. 1F) or the plasma histamine levels (FIG. 1G), 30 minutes after challenge at week 5 in peanut allergic (n=3) and control mice (n=3).

Figure 1H:
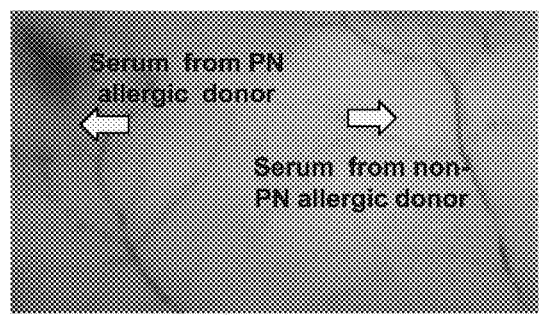

FIG. 1H is an image illustrating passive cutaneous anaphylaxis in the skin of a mouse, wherein reactions produced a visible blue color indicated in the Figure. Abdomens of naive Balb/C mice were shaved 1 day before intradermal injection of 50 μl of pooled sera from NSG mice reconstituted with blood mononuclear cells from a peanut allergic individual or from a control donor sensitized and challenged with peanut extract at week 7.5. Twenty-four hours after intradermal administration of the sera, mice were administered intravenously a mixture of 100 μl of 0.5% Evan's blue dye and 100 μg peanut extract. After 30 min, mice were sacrificed, the skin of the abdomen inverted, and reactions examined by visible blue color.

Figure 2A:
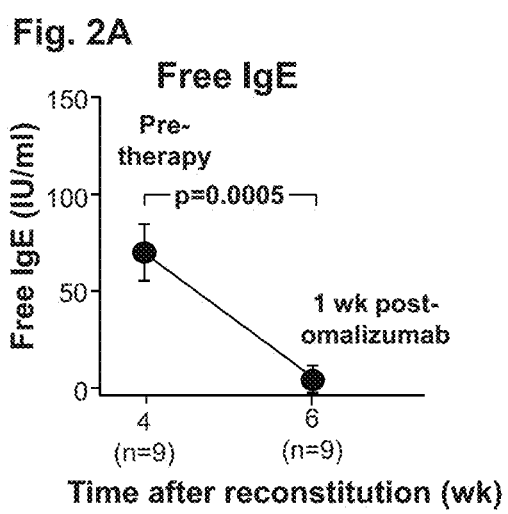
Figure 2B:
Figure 2C:

FIGS. 2A-2C depict experimental data illustrating the effectiveness of omalizumab treatment for peanut antigen-induced anaphylaxis in NSG mice after sensitization and challenge. FIG. 2A is a graph showing the free IgE levels measured by ELISA 1 week prior to therapy and 1 week after therapy with omalizumab (n=9). FIG. 2B is an image of a mouse treated with omalizumab that appeared normal after peanut challenge, and FIG. 2C is an image depicting omalizumab-mediated suppression of passive cutaneous anaphylaxis.

Figure 3A:
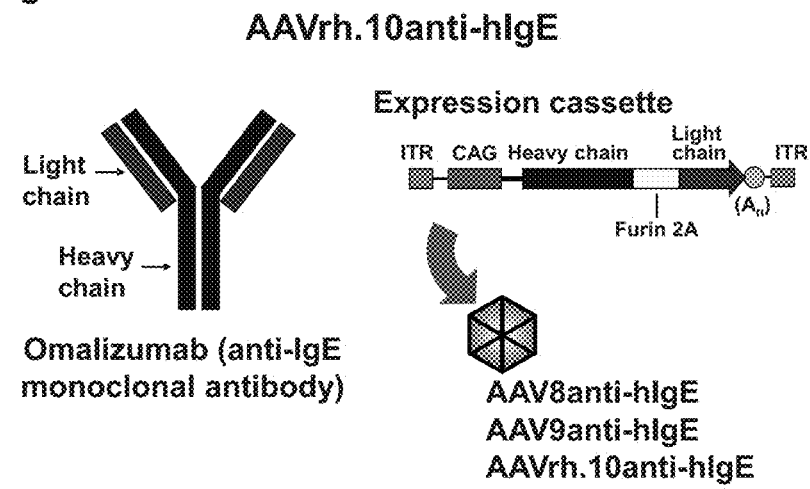

FIG. 3A is a schematic drawing of the AAVrh.10anti-hIgE vector, which shows the CMV enhancer/chicken beta-actin (CAG) promoter, heavy and light chain of the anti-IgE monoclonal antibody omalizumab, furin 2A cleavage site, and polyadenylation signal.

Figure 3B:
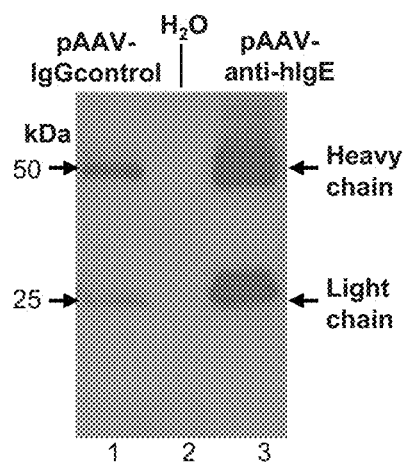

FIG. 3B is an image of a Western blot which depicts expression of the anti-IgE antibody encoded by the AAVrh.10anti-hIgE vector in HEK 293 cells.

FIG. 3C is a graph of experimental data illustrating the persistent expression of the anti-IgE antibody over time following single intravenous administration of AAVrh.10anti-hIgE or AAVrh.10IgGcontrol to NSG mice (n=5).

Figure 3D:
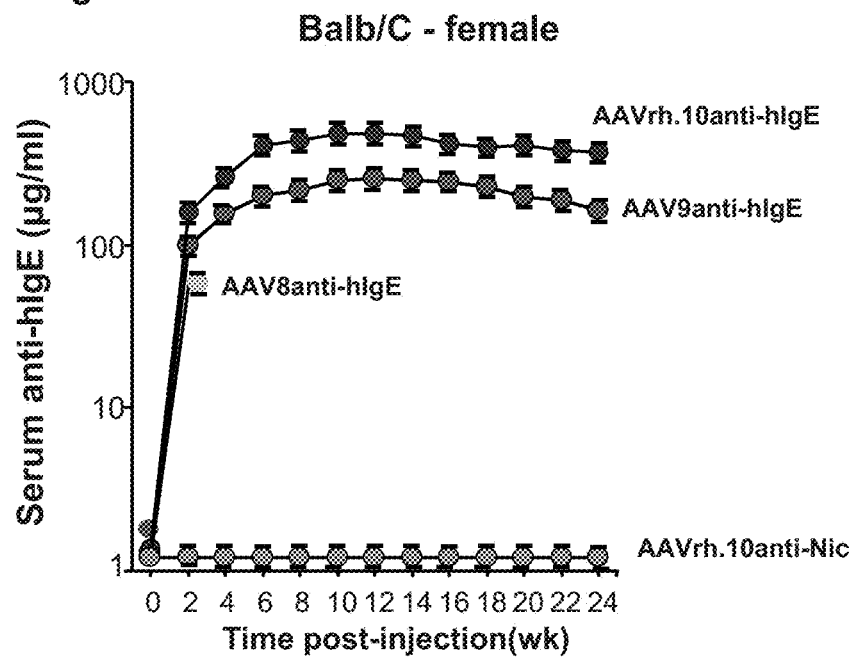

FIG. 3D is a graph of experimental data illustrating the persistent expression of the anti-IgE antibody over time following single intravenous administration of AAVrh.10anti-hIgE, AAV9anti-hIgE, AAV8anti-hIgE, or AAVrh.10anti-nicotine (control) to Balb/C female mice (n=5/group).

Figure 3E:
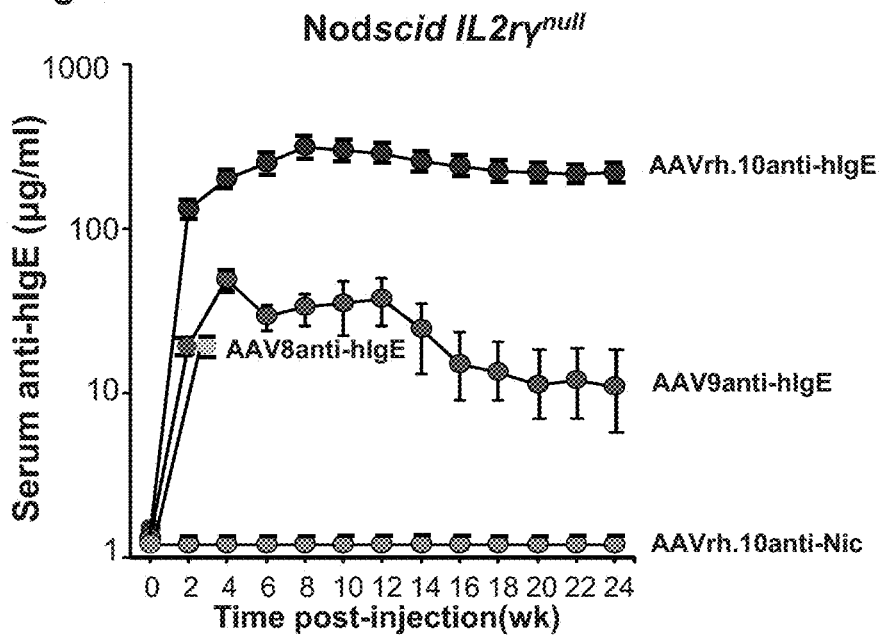

FIG. 3E is a graph of experimental data illustrating the persistent expression of the anti-IgE antibody over time following single intravenous administration of AAVrh.10anti-hIgE, AAV9anti-hIgE, AAV8anti-hIgE, or AAVrh.10anti-nicotine (control) to NSG female mice (n=5/group).

Figure 4A:
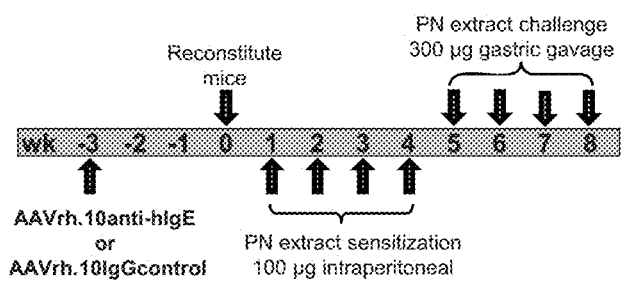

FIG. 4A is a schematic illustration of the therapeutic protocol for testing prophylactic treatment of NSG mice.

Figure 4B:
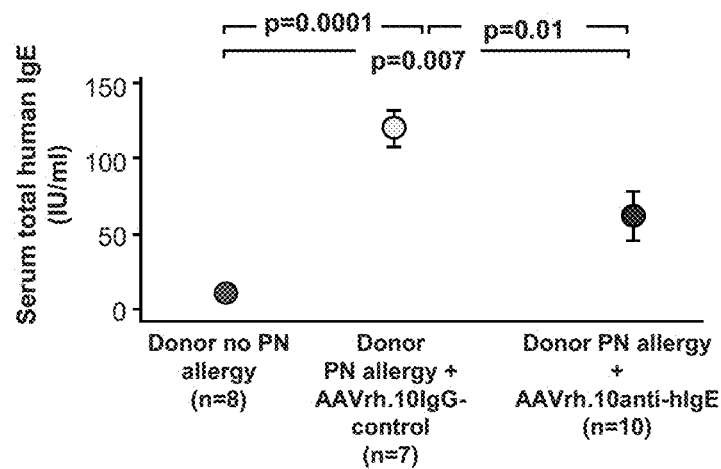

FIGS. 4 B-4D are graphs of experimental data illustrating the levels of total human IgE (FIG. 4B), total peanut-specific IgE (FIG. 4C) and free IgE (FIG. 4D) in NOD-scid-IL2Rgamma$^{null}$ (NSG) mice reconstituted with human blood mononuclear cells from a peanut allergic treated with the AAVrh.10anti-hIgE vector or the AAVrh.10anti-hIgG control vector or mice reconstituted with human blood mononuclear cells from a control donor, as measured by ELISA (mean±SEM, Figures B and C; n=8 donors with no PN allergy, n=7 donor with PN allergy+AAVrh.10IgGcontrol, n=10 donor with PN allergy+AAVrh.10anti-hIgE, Figure C; n-8 donor no PN allergy, n=7 donor with PN allergy+AAVrh.10IgGcontrol, n=10 donor with PN allergy+AAVrh.10anti-hIgE).

Figure 5A:
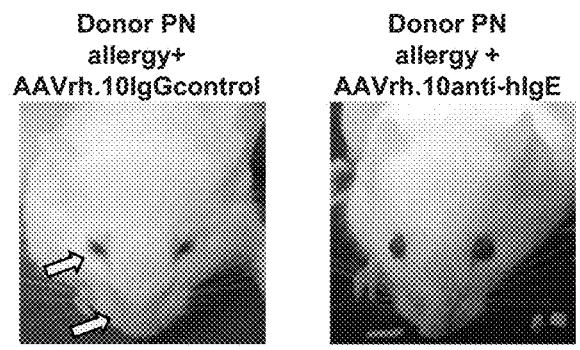

FIG. 5A provides images of mice after peanut extract challenge at week 6. Left—mouse treated with a control vector at week-3 displayed puffiness around eyes/snout and pilar erecti, itching/ruffling of fur, decreased ambulation and respiratory rate after peanut challenge. Right—mouse, treated with AAVrh.10anti-hIgE at week-3 appeared normal after peanut challenge.

Figure 5B:
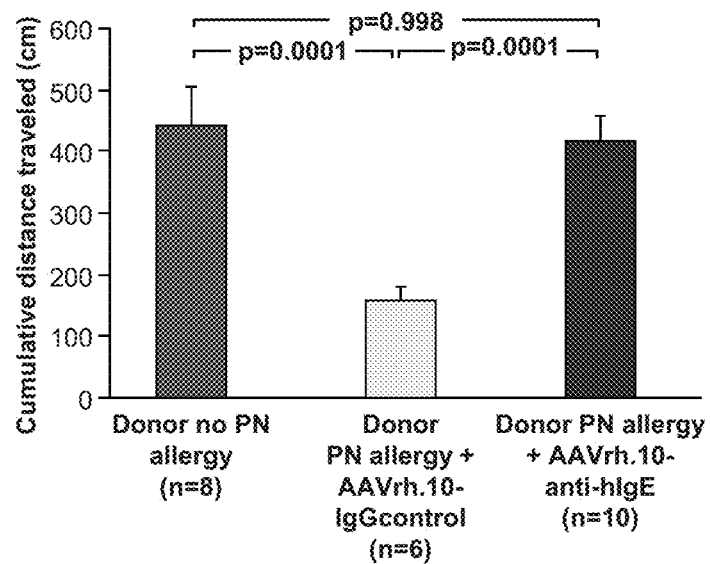

FIGS. 5B-5E are graphs and images depicting changes in anaphylaxis after AAVrh.10anti-hIgE treatment. FIG. 5B depicts locomotor activity based on infrared-beam open-field chamber box assessment of cumulative distance traveled. Shown is the distance transversed over the following 30 min in vector and control treated mice assessed at week 6 (n=8 donors with no PN allergy, n=6 donor with PN allergy+AAVrh.10IgGcontrol, n=10 donor with PN allergy+AAVrh.10anti-hIgE).

FIG. 5C depicts anaphylaxis score, 30 min after peanut challenge at week 6 (n=8 donor with no PN allergy, n=6 donor with PN allergy+AAVrh.10IgGcontrol, n=10 donor with PN allergy+AAVrh.10anti-hIgE).

FIG. 5D depicts plasma histamine levels 30 min after peanut challenge at week 7 (n=7 donors with no PN allergy, n=6 donor with PN allergy+AAVrh.10IgGcontrol, n=10 donor with PN allergy+AAVrh.10anti-hIgE).

Figure 5E:
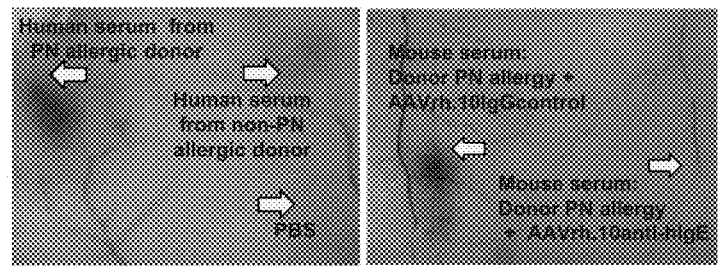

FIG. 5E depicts the AAVrh.10anti-hIgE-mediated suppression of passive cutaneous anaphylaxis: Left panel—Peanut extract-induced passive cutaneous anaphylaxis mediated by the peanut-specific IgE from the serum of a peanut allergic donor; Right panel—Peanut extract induced passive cutaneous anaphylaxis-mediated by the peanut specific IgE from the pooled serum of the humanized peanut allergic NSG mice reconstituted using the same donor as in left panel, but treated prophylactically with AAVrh.10anti-hIgE 3 weeks before sensitization. The sera from the AAVrh.10anti-hIgE treated mice blocked peanut induced peanut-specific IgE-mediated passive cutaneous anaphylaxis compared to the AAVrh.10IgGcontrol.

Figure 6A:
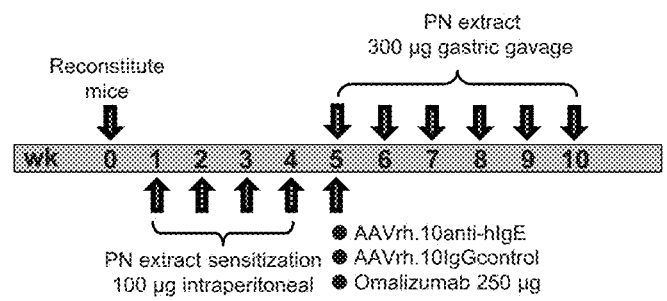
Figure 6B:
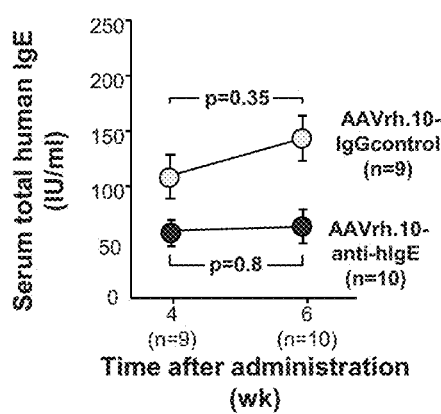

FIG. 6A is a schematic illustration of the therapeutic protocol for testing therapeutic treatment of peanut induced anaphylaxis in the NSG mice. FIGS. 6B-6D are graphs of experimental data illustrating the levels of total human IgE (FIG. 6B), total peanut-specific IgE (FIG. 6C) and free IgE (FIG. 6D) in NSG mice reconstituted with human blood mononuclear cells from a peanut allergic individual treated with the AAVrh.10anti-hIgE vector or the AAVrh.10anti-hIgGcontrol vector, as measured by ELISA (mean±SEM).

Figure 7A:
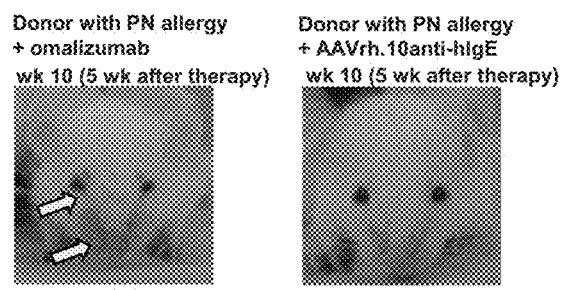

FIG. 7A provides images of mice after peanut extract challenge at week 10: Left panel—mouse treated with omalizumab displayed puffiness around eyes/snout and pilar erecti, itching/ruffling of fur, decreased ambulation and respiratory rate after peanut challenge; Right panel—mouse, treated with AAVrh.10anti-hIgE at week 10 (5 weeks after therapy) appeared normal after peanut challenge.

Figure 7B:
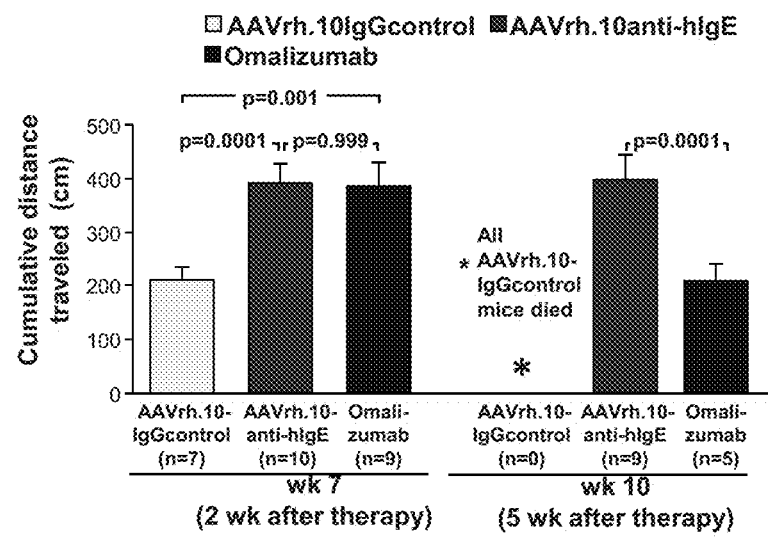

FIGS. 7B-7E are graphs and images depicting changes in anaphylaxis after AAVrh.10anti-hIgE treatment. FIG. 7B depicts locomotor activity based on infrared-beam open-field chamber box assessment of cumulative distance traveled, starting 30 min after peanut challenge in vector, control treated and omalizumab mice. Shown is data of the distance transversed over the next 30 min for week 7 (i.e., 2 weeks after therapy) and week 10 (i.e., 5 weeks after therapy). Week 7 data n=10 for AAVrh.10anti-hIgE, n=9 for omalizumab, and n=7 for AAVrh.10IgGcontrol, and Week 10 data n=9 for AAVrh.10anti-hIgE, n=5 for omalizumab, and n=0 for AAVrh.10IgGcontrol.

Figure 7C:
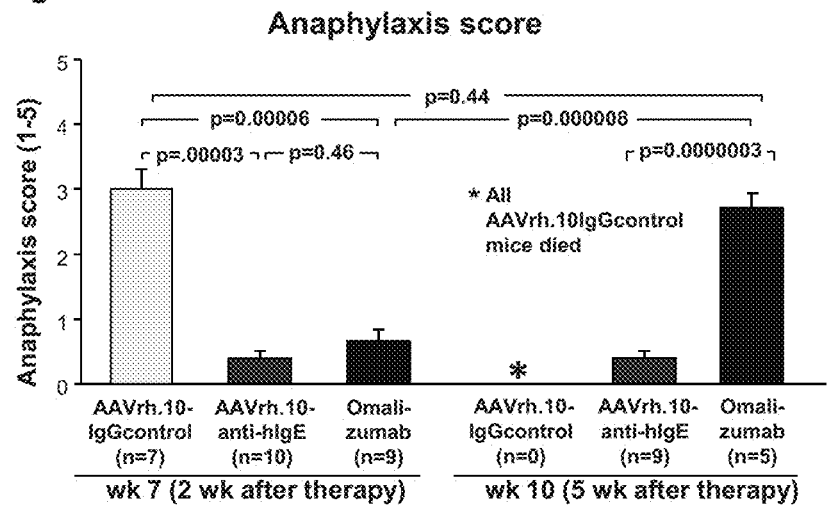

FIG. 7C depicts the anaphylaxis score, 30 min after peanut challenge. Shown is data for week 7 (i.e., 2 weeks after therapy) and week 10 (i.e., 5 weeks after therapy). Week 7 data n=10 for AAVrh.10anti-hIgE, n=9 for omalizumab, and n=7 for AAVrh.10IgGcontrol. Week 10 data n=9 for AAVrh.10anti-hIgE, n=5 for omalizumab, and n=0 for AAVrh.10IgGcontrol.

Figure 7D:
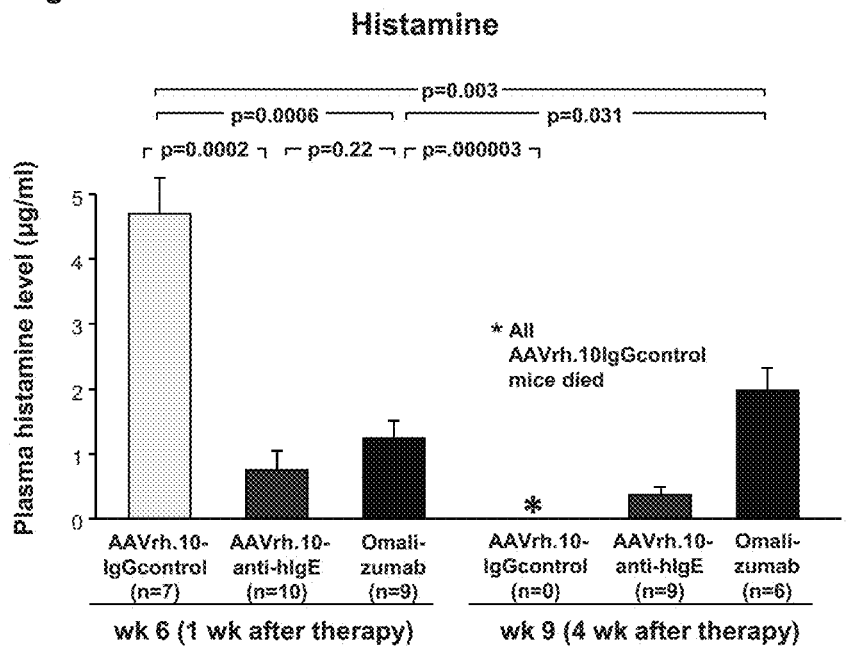

FIG. 7D depicts plasma histamine levels 30 min after peanut challenge. Shown is data for week 6 (i.e., 1 week after therapy) and week 9 (i.e., 4 weeks after therapy). Week 6 data n=10 for AAVrh.10anti-hIgE, n=9 for omalizumab, and n=7 AAVrh.10IgGcontrol. Week 9 data n=9 for AAVrh.10anti-hIgE, n=6 omalizumab, and n=0 AAVrh.10IgGcontrol.

Figure 7E:
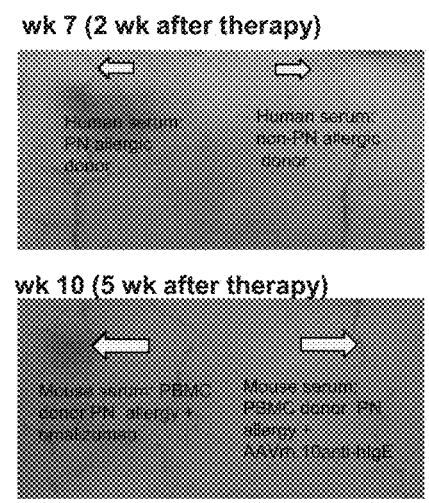

FIG. 7E depicts the AAVrh.10 anti-hIgE-mediated suppression of passive cutaneous anaphylaxis. Top panel—week 7 (2 weeks after therapy) peanut extract-induced passive cutaneous anaphylaxis mediated by the peanut-specific IgE from the serum of a peanut allergic donor, but not from a non-allergic control. Bottom panel—week 10 (i.e., 5 weeks after therapy) persistent expression of AAVrh.10anti-hIgE blocks extravasation of dye, whereas a one-time injection of omalizumab 5 weeks prior was no longer protective.

FIG. 8 is a graph which depicts mouse survival following treatment with AAVrh.10anti-hIgE, omalizumab alone or control vector. Survival duration and treatment type are shown days post-therapy.

DETAILED DESCRIPTION OF THE INVENTION

The invention provides gene therapy vectors and methods of using the same to provide persistent expression of a therapeutic transgene to inhibit or reduce an immune response or allergic reaction to an allergen in a mammal. The vector comprises, consists essentially of, or consists of a promoter operably linked to a nucleic acid sequence that encodes an anti-IgE antibody or antigen binding fragment thereof, or encodes a soluble IgE receptor, an eosinophil, a basophil, IL-13, or IL-4. The vector can comprise additional components that do not materially affect the vector (e.g., genetic elements such as poly(A) sequences or restriction enzyme sites that facilitate manipulation of the vector in vitro). However, in some embodiments, the vector does not comprise any additional components (i.e., components that are not endogenous to the vector and are not required to effect expression of the nucleic acid sequence to thereby provide the antibody).

The vector of the invention can comprise, consist essentially of, or consist of any gene transfer vector known in the art. Examples of such vectors include adeno-associated viral (AAV) vectors, adenoviral vectors, lentiviral vectors, retroviral vectors, and plasmids. In a preferred embodiment the vector is an AAV vector.

Adeno-associated virus is a member of the Parvoviridae family and comprises a linear, single-stranded DNA genome of less than about 5,000 nucleotides. AAV requires co-infection with a helper virus (i.e., an adenovirus or a herpes virus), or expression of helper genes, for efficient replication. AAV vectors used for administration of therapeutic nucleic acids typically have approximately 96% of the parental genome deleted, such that only the terminal repeats (ITRs), which contain recognition signals for DNA replication and packaging, remain. This eliminates immunologic or toxic side effects due to expression of viral genes. In addition, delivering specific AAV proteins to producing cells enables integration of the AAV vector comprising AAV ITRs into a specific region of the cellular genome, if desired (see, e.g., U.S. Pat. Nos. 6,342,390 and 6,821,511). Host cells comprising an integrated AAV genome show no change in cell growth or morphology (see, for example, U.S. Pat. No. 4,797,368).

The AAV ITRs flank the unique coding nucleotide sequences for the non-structural replication (Rep) proteins and the structural capsid (Cap) proteins (also known as virion proteins (VPs)). The terminal 145 nucleotides are self-complementary and are organized so that an energetically stable intramolecular duplex forming a T-shaped hairpin may be formed. These hairpin structures function as an origin for viral DNA replication by serving as primers for the cellular DNA polymerase complex. The Rep genes encode the Rep proteins Rep78, Rep68, Rep52, and Rep40. Rep78 and Rep68 are transcribed from the p5 promoter, and Rep 52 and Rep40 are transcribed from the p19 promoter. The Rep78 and Rep68 proteins are multifunctional DNA binding proteins that perform helicase and nickase functions during productive replication to allow for the resolution of AAV termini (see, e.g., Im et al., *Cell*, 61: 447-57 (1990)). These proteins also regulate transcription from endogenous AAV promoters and promoters within helper viruses (see, e.g., Pereira et al., *J. Virol.*, 71: 1079-1088 (1997)). The other Rep proteins modify the function of Rep78 and Rep68. The cap genes encode the capsid proteins VP1, VP2, and VP3. The cap genes are transcribed from the p40 promoter.

The inventive AAV vector can be generated using any AAV serotype known in the art. Several AAV serotypes and over 100 AAV variants have been isolated from adenovirus stocks or from human or nonhuman primate tissues (reviewed in, e.g., Wu et al., *Molecular Therapy*, 14(3): 316-327 (2006)). Generally, the AAV serotypes have genomic sequences of significant homology at the nucleic acid sequence and amino acid sequence levels, such that different serotypes have an identical set of genetic functions, produce virions which are essentially physically and functionally equivalent, and replicate and assemble by practically identical mechanisms. AAV serotypes 1-6 and 7-9 are defined as "true" serotypes, in that they do not efficiently cross-react with neutralizing sera specific for all other existing and characterized serotypes. In contrast, AAV serotypes 6, 10 (also referred to as Rh10), and 11 are considered "variant" serotypes as they do not adhere to the definition of a "true" serotype. AAV serotype 2 (AAV2) has been used extensively for gene therapy applications due to its lack of pathogenicity, wide range of infectivity, and ability to establish long-term transgene expression (see, e.g., Carter, B. J., *Hum. Gene Ther.*, 16: 541-550 (2005); and Wu et al., supra). Genome sequences of various AAV serotypes and comparisons thereof are disclosed in, for example, GenBank Accession numbers U89790, J01901, AF043303, and AF085716; Chiorini et al., *J. Virol.*, 71: 6823-33 (1997); Srivastava et al., *J. Virol.*, 45: 555-64 (1983); Chiorini et al., *J. Virol.*, 73: 1309-1319 (1999); Rutledge et al., *J. Virol.*, 72: 309-319 (1998); and Wu et al., *J. Virol.*, 74: 8635-47 (2000)).

AAV rep and ITR sequences are particularly conserved across most AAV serotypes. For example, the Rep78 proteins of AAV2, AAV3A, AAV3B, AAV4, and AAV6 are reportedly about 89-93% identical (see Bantel-Schaal et al., *J. Virol.*, 73(2): 939-947 (1999)). It has been reported that AAV serotypes 2, 3A, 3B, and 6 share about 82% total nucleotide sequence identity at the genome level (Bantel-Schaal et al., supra). Moreover, the rep sequences and ITRs of many AAV serotypes are known to efficiently cross-complement (i.e., functionally substitute) corresponding sequences from other serotypes during production of AAV particles in mammalian cells.

Generally, the cap proteins, which determine the cellular tropicity of the AAV particle, and related cap protein-encoding sequences, are significantly less conserved than Rep genes across different AAV serotypes. In view of the ability Rep and ITR sequences to cross-complement corresponding sequences of other serotypes, the AAV vector can comprise a mixture of serotypes and thereby be a "chimeric" or "pseudotyped" AAV vector. A chimeric AAV vector typically comprises AAV capsid proteins derived from two or more (e.g., 2, 3, 4, etc.) different AAV serotypes. In contrast, a pseudotyped AAV vector comprises one or more ITRs of one AAV serotype packaged into a capsid of another AAV serotype. Chimeric and pseudotyped AAV vectors are further described in, for example, U.S. Pat. No. 6,723,551; Flotte, *Mol. Ther.*, 13(1): 1-2 (2006); Gao et al., *J. Virol.*, 78: 6381-6388 (2004); Gao et al., *Proc. Natl. Acad. Sci. USA*, 99: 11854-11859 (2002); De et al., *Mol. Ther.*, 13: 67-76 (2006); and Gao et al., *Mol. Ther.*, 13: 77-87 (2006).

In one embodiment, the AAV vector is generated using an AAV that infects humans (e.g., AAV2). In a preferred embodiment the AAV vector generated using an AAV that infects humans is AAV8 or AAV9. Alternatively, the AAV vector is generated using an AAV that infects non-human primates, such as, for example, the great apes (e.g., chimpanzees), Old World monkeys (e.g., macaques), and New World monkeys (e.g., marmosets). Preferably, the AAV vector is generated using an AAV that infects a non-human primate pseudotyped with an AAV that infects humans. Examples of such pseudotyped AAV vectors are disclosed in, e.g., Cearley et al., *Molecular Therapy*, 13: 528-537 (2006). In one embodiment, an AAV vector can be generated which comprises a capsid protein from an AAV that infects rhesus macaques pseudotyped with AAV2 inverted terminal repeats (ITRs).

In a particularly preferred embodiment, the inventive AAV vector comprises a capsid protein from AAV10 (also referred to as "AAVrh.10"), which infects rhesus macaques pseudotyped with AAV2 ITRs (see, e.g., Watanabe et al., *Gene Ther.*, 17(8): 1042-1051 (2010); and Mao et al., *Hum. Gene Therapy*, 22: 1525-1535 (2011)).

The inventive vector comprises a promoter operably linked to a nucleic acid sequence that encodes an anti-IgE antibody or antigen binding fragment thereof, or encodes a soluble IgE receptor, an eosinophil, a basophil, IL-13, or IL-4. DNA regions are "operably linked" when they are functionally related to each other. A promoter is "operably linked" to a coding sequence if it controls the transcription of the sequence.

A "promoter" is a region of DNA that initiates transcription of a particular gene. A large number of promoters from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction).

The promoter of the inventive vector can comprise, consist essentially of, or consist of any promoter known in the art. Examples of classes of such promoters include constitutively active promoters (e.g., human beta-actin, chicken beta-actin, cytomegalovirus (CMV), and SV40), cell type specific promoters (e.g., CD19 gene promoter, CaMKIIa, and UAS), or an inducible promoter (e.g., the Tet system (U.S. Pat. Nos. 5,464,758 and 5,814,618), the Ecdysone inducible system (No et al., *Proc. Natl. Acad. Sci.*, 93: 3346-3351 (1996)), the T-REX' system (Invitrogen, Carlsbad, Calif.), the Cre-ERT tamoxifen inducible recombinase system (Indra et al., *Nuc. Acid. Res.*, 27: 4324-4327 (1999); *Nuc. Acid. Res.*, 28: e99 (2000); U.S. Pat. No. 7,112,715; and Kramer & Fussenegger, *Methods Mol. Biol.*, 308: 123-144 (2005)), and the LACSWITCH™ System (Stratagene, San Diego, Calif.)).

In a preferred embodiment of the invention the promoter is a constitutively active promoter, an inducible promoter, or a cell-type specific promoter. One example of a promoter is the chicken beta-actin promoter.

"Nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides.

The nucleic acid sequence operably linked to the promoter may comprise any nucleic acid sequence that encodes a therapeutic gene which blocks allergic reactions. The nucleic acid sequence preferably encodes an anti-IgE antibody or antigen binding fragment thereof, a soluble IgE receptor, an eosinophil, a basophil, IL-13, or IL-4. The nucleic acid sequence may also encode for fusion proteins which are comprised of an active protein e.g., the soluble IgE receptor, an eosinophil, a basophil, IL-13, IL-4, or any therapeutic gene which blocks allergic reactions and a second moiety, usually a protein, which improves the properties (e.g., efficacy, solubility, or half-life) of the active protein. Examples of the second moiety are known in the art and include, for example, the Fc domain of an immunoglobulin and polyethylene glycol (PEG). In one embodiment, the nucleic acid sequence operably linked to the promoter encodes only an anti-IgE antibody or antigen binding fragment thereof.

One of ordinary skill in the art will appreciate that an antibody consists of four polypeptides: two identical copies of a heavy (H) chain polypeptide and two copies of a light (L) chain polypeptide. Each of the heavy chains contains one N-terminal variable ($V_H$) region and three C-terminal constant ($C_H1$, $C_H2$ and $C_H3$) regions, and each light chain contains one N-terminal variable ($V_L$) region and one C-terminal constant ($C_L$) region. The variable regions of each pair of light and heavy chains form the antigen binding site of an antibody. The inventive vector can comprise one or more nucleic acid sequences, each of which encodes one or more of the heavy and/or light chain polypeptides of an anti-IgE antibody. In this respect, the inventive vector can comprise a single nucleic acid sequence that encodes the two heavy chain polypeptides and the two light chain polypeptides of an anti-IgE antibody. Alternatively, the inventive vector can comprise a first nucleic acid sequence that encodes both heavy chain polypeptides of an anti-IgE antibody, and a second nucleic acid sequence that encodes both light chain polypeptides of an anti-IgE antibody. In yet another embodiment, the inventive vector can comprise a first nucleic acid sequence encoding a first heavy chain polypeptide of an anti-IgE antibody, a second nucleic acid sequence encoding a second heavy chain polypeptide of an anti-IgE antibody, a third nucleic acid sequence encoding a first light chain polypeptide of an anti-IgE antibody, and a fourth nucleic acid sequence encoding a second light chain polypeptide of an anti-IgE antibody.

In another embodiment, the vector can comprise a nucleic acid sequence that encodes an antigen-binding fragment (also referred to as an "antibody fragment") of an anti-IgE antibody. The term "antigen-binding fragment" refers to one or more fragments of an antibody that retain the ability to specifically bind to an antigen (e.g., immunoglobulin E) (see, generally, Holliger et al., *Nat. Biotech.*, 23(9): 1126-1129 (2005)). Examples of antigen-binding fragments include but are not limited to (i) a Fab fragment, which is a monovalent fragment consisting of the $V_L$, $V_H$, $C_L$, and $C_H1$ domains; (ii) a F(ab')$_2$ fragment, which is a bivalent fragment comprising two Fab fragments linked by a disulfide bridge at the hinge region; and (iii) a Fv fragment consisting of the $V_L$ and $V_H$ domains of a single arm of an antibody. In one embodiment, the vector can comprise a nucleic acid sequence encoding a Fab fragment of an anti-IgE antibody.

The nucleic acid sequence can encode any anti-IgE antibody or antigen binding fragment thereof known in the art. In one embodiment, the nucleic acid sequence can encode an anti-IgE antibody or antigen binding fragment thereof comprising a heavy chain polypeptide comprising three complimentarity determining regions (CDRs), wherein CDR-H1 comprises the nucleic acid sequence of SEQ ID NO: 1, CDR-H2 comprises the nucleic acid sequence of SEQ ID NO: 2, and CDR-H3 comprises the nucleic acid sequence of SEQ ID NO: 3, and a light chain polypeptide comprising three CDRs, wherein CDR-L1 comprises the nucleic acid sequence of SEQ ID NO: 4, CDR-L2 comprises the nucleic acid sequence of SEQ ID NO: 5, and CDR-L3 comprises the nucleic acid sequence of SEQ ID NO: 6.

In another embodiment, the nucleic acid sequence can encode an anti-IgE antibody or antigen binding fragment thereof comprising a heavy chain variable region comprising SEQ ID NO: 7 and a light chain variable region comprising SEQ ID NO: 8.

In another embodiment, the nucleic acid sequence encodes an anti-IgE antibody or antigen binding fragment thereof comprising SEQ ID NO: 9.

In another embodiment, the nucleic acid sequence can encode an anti-IgE antibody or antigen binding fragment thereof comprising the high-affinity, IgE-binding monoclonal antibody omalizumab (see, e.g., U.S. Pat. No. 6,682,735) or antigen-binding fragment thereof, or an anti-IgE antibody or antibody fragment that binds to the same epitope as omalizumab. In this respect, the inventive vector can comprise a nucleic acid sequence encoding full-length heavy and light chain polypeptides of omalizumab (e.g., SEQ ID NO: 10 and SEQ ID NO: 11, respectively).

An antibody, or antigen-binding fragment thereof, can be obtained by any means, including via in vitro sources (e.g., a hybridoma or a cell line producing an antibody recombinantly) and in vivo sources (e.g., rodents). Methods for generating antibodies are known in the art and are described in, for example, Köhler and Milstein, *Eur. J. Immunol.*, 5: 511-519 (1976); Harlow and Lane (eds.), *Antibodies: A Laboratory Manual*, CSH Press (1988); and C. A. Janeway et al. (eds.), *Immunobiology*, 5th Ed., Garland Publishing, New York, N.Y. (2001)). In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the HUMAB-MOUSE™, the Kirin TC MOUSE™, and the KM-MOUSE™ (see, e.g., Lonberg, *Nat. Biotechnol.*, 23(9): 1117-25 (2005), and Lonberg, *Handb. Exp. Pharmacol.*, 181: 69-97 (2008)).

The nucleic acid sequence encoding the anti-IgE antibody, or an antigen-binding fragment thereof, can be generated using methods known in the art. For example, nucleic acid sequences, polypeptides, and proteins can be recombinantly produced using standard recombinant DNA methodology (see, e.g., Sambrook et al., *Molecular Cloning: A Laboratory Manual*, 3$^{rd}$ ed., Cold Spring Harbor Press, Cold Spring Harbor, N.Y., 2001; and Ausubel et al., *Current Protocols in Molecular Biology*, Greene Publishing Associates and John Wiley & Sons, N Y, 1994). Further, a synthetically produced nucleic acid sequence encoding an anti-IgE antibody, or an antigen-binding fragment thereof, can be isolated and/or purified from a source, such as a bacterium, an insect, or a mammal, e.g., a rat, a human, etc. Methods of isolation and purification are well-known in the art. Alternatively, the nucleic acid sequences described herein can be commercially synthesized. In this respect, the nucleic acid sequence can be synthetic, recombinant, isolated, and/or purified.

In addition to the promoter operably linked to a nucleic acid sequence encoding an anti-IgE antibody or antigen-binding fragment thereof, soluble IgE receptor, an eosinophil, a basophil, IL-13, or IL-4, the vector can comprise additional expression control sequences, such as enhancers, polyadenylation signals, transcription terminators, internal ribosome entry sites (IBES), and the like, that provide for the expression of the nucleic acid sequence in a host cell. Exemplary expression control sequences are known in the art and described in, for example, Goeddel, *Gene Expression Technology: Methods in Enzymology*, Vol. 185, Academic Press, San Diego, Calif. (1990).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. The nucleic acid sequence encoding the anti-IgE antibody or antigen-binding fragment thereof, soluble IgE receptor, an eosinophil, a basophil, IL-13, or IL-4 may be operably linked to a CMV enhancer/chicken β-actin promoter (also referred to as a "CAG promoter") (see, e.g., Niwa et al., *Gene*, 108: 193-199 (1991); Daly et al., *Proc. Natl. Acad. Sci. U.S.A.*, 96: 2296-2300 (1999); and Sondhi et al., *Mol. Ther.*, 15: 481-491 (2007)).

The invention provides a composition comprising, consisting essentially of, or consisting of the above-described vector and a pharmaceutically acceptable (e.g. physiologically acceptable) carrier. When the composition consists essentially of the inventive vector and a pharmaceutically acceptable carrier, additional components can be included that do not materially affect the composition (e.g., adjuvants, buffers, stabilizers, anti-inflammatory agents, solubilizers, preservatives, etc.). When the composition consists of the inventive vector and the pharmaceutically acceptable carrier, the composition does not comprise any additional components. Any suitable carrier can be used within the context of the invention, and such carriers are well known in the art. The choice of carrier will be determined, in part, by the particular site to which the composition may be administered and the particular method used to administer the composition. The composition optionally can be sterile with the exception of the vector described herein. The composition can be frozen or lyophilized for storage and reconstituted in a suitable sterile carrier prior to use. The compositions can be generated in accordance with conventional techniques described in, e.g., *Remington: The Science and Practice of Pharmacy*, 21st Edition, Lippincott Williams & Wilkins, Philadelphia, Pa. (2001).

Suitable formulations for the composition include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. Preferably, the carrier is a buffered saline solution. More preferably, the inventive vector is administered in a composition formulated to protect the inventive vector from damage prior to administration. For example, the composition can be formulated to reduce loss of the vector on devices used to prepare, store, or administer the vector, such as glassware, syringes, or needles. The composition can be formulated to decrease the light sensitivity and/or temperature sensitivity of the vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the vector, facilitate administration, and increase the efficiency of the inventive method. Formulations for vector-containing compositions are further described in, for example, Wright et al., *Curr. Opin. Drug Discov. Devel.*, 6(2): 174-178 (2003) and Wright et al., *Molecular Therapy*, 12: 171-178 (2005))

The composition also can be formulated to enhance transduction efficiency. In addition, one of ordinary skill in the art will appreciate that the inventive vector can be present in a composition with other therapeutic or biologically-active agents. For example, factors that control inflammation, such as ibuprofen or steroids, can be part of the composition to reduce swelling and inflammation associated with in vivo administration of the vector. Antibiotics, i.e., microbicides and fungicides, can be present to treat existing infection and/or reduce the risk of future infection, such as infection associated with gene transfer procedures.

The invention provides a method of inhibiting or reducing an immune response or allergic reaction to an allergen in a mammal comprising administering the inventive vector to the mammal, whereupon the nucleic acid is expressed to produce the protein that inhibits or reduces the immune response. In a preferred embodiment the mammal is a human.

Inhibiting or reducing an immune response or allergic reaction to an allergen encompasses any degree of amelioration of any physiological response to an allergen. Non-limiting examples of physiological responses include hives, rashes, mucus production, and anaphylaxis. In a preferred embodiment the immune response or allergic reaction reduced or inhibited by the method is anaphylaxis.

The allergen of the present invention may be any allergen that causes an allergic reaction in a mammal. Non-limiting examples of allergens that can be treated by the inventive method include:

Food allergens, such as, peanuts, tree nuts (hazelnut, almond, cashew, macadamia, pistachio, pine nut, walnut, brazil nut, chestnut, pecan) fish/crustacean/shellfish (sole, squid, mackerel, codfish, blue mussel, mahi mahi, pike, halibut, tuna, mackerel, salmon, trout, codfish, anchovy, pollock, catfish, red snapper, herring, flounder, salmon, trout, swordfish, whitefish, oyster, scallop, sardine, crayfish, haddock, tilapia, crab, shrimp, clam, bass, octopus), soy, milk/dairy (goat milk, cow milk etc), wheat, gluten, sulfites, sesame, garlic, oats, whey, dill, basil, thyme, yam, sage, lime, clove, mint, honey, oregano, nutmeg, sugar beet, poppy seed, orris root, ginger, cucumber, asparagus, cranberry, zucchini, raspberry, red currant, rosemary, ovalbumin, artichoke, black bean, cumin seed, nectarine, apple, plum, banana, turmeric, mandarin, *quinoa*, pumpkin, black olive, green olive, fungi/mold (cheese mold/food mold), orange, corn, watermelon, carrot, potato, lima bean, white bean, pea, pepper, fennel, summer squash, sunflower seed, green bean, caraway seed, cardamom seed, carob (gum)/locust bean, gelatin (porcine, bovine, fish) pumpkin seed, flaxseed/linseed, coriander/cilantro, blackberry, annatto seed, common millet, cauliflower, canola oil, chickpea (garbanzo bean), grape, tomato, kiwi, *papaya*, celery, avocado, buckwheat, alpha-gal, rice, chocolate, chicken, turkey, lamb, navy bean, rye, barley, casein, cabbage, lettuce, pepper, beef/meat pork, mango, pear, spinach, egg white, egg yolk, egg-whole, *papaya*, coconut, apricot, blueberry, honeydew, melon, cantaloupe, mustard, tea, vanilla, lemon, lime, broccoli, cinnamon, onion, pineapple, garlic, grapefruit, lentil, malt, coffee, mushroom, jalapenos, cocoa, food additives (baker's yeast, ascorbic acid, aspartame, nitrates, guar, MSG, carrageenan);

Medications such as, β Lactam antibiotics: Penicillin, amoxicillin, ampicillin, Penicillin G, Penicillin V etc, cephalosoprins, monobactams, carbapenems, non β Lactam antibiotics, anti-mycobacterial drugs, diabetes medications, cancer chemotherapeutic agents, HIV medications, immunomodulatory agents for autoimmune diseases, modifying drugs for dermatologic diseases, perioperative agents, opiates, corticosteroids, protamine, Heparin (anti-coagulants), local anesthetics, radiocontrast media, aspirin and nonsteroidal anti-inflammatory drugs (NSAIDs), angiotensin-converting enzyme (ACE) inhibitors, biologic modifiers, cytokines, anti-TNF-drugs, monoclonal antibodies, anticancer monoclonal antibodies, complementary medicines, anti-seizure medications;

Environmental allergens such as Tree Pollens, Cat (dander), Dog (dander), guinea pig, duck feathers, chicken feathers, goose feathers, horse (hair/dander), guinea pig (epithelium), pig/swine (epithelium) goat epithelium, hamster (epithelium), mouse (epithelium), bird droppings/stools, insects/venom (honeybee, white faced hornet, paper wasp, yellow-faced hornet, yellow jacket, fire ant, ant etc), mold/fungus, dust mites, house dust, latex, grass, mites, weeds trees, cockroach; and Other common allergens such as semen/seminal fluid, blood and blood products.

Preferably the allergen is a food allergen (e.g. shrimp or seafood, peanut, or tree nut), pollen, dust mite, or insect venom, such as bee sting venom.

Any route of administration can be used to deliver the composition to the mammal. Indeed, although more than one route can be used to administer the composition, a particular route can provide a more immediate and more effective reaction than another route. Preferably, the composition is administered via intramuscular injection. A dose of composition also can be applied or instilled into body cavities, absorbed through the skin (e.g., via a transdermal patch), inhaled, ingested, topically applied to tissue, or administered parenterally via, for instance, intravenous, intraperitoneal, intraoral, intradermal, subcutaneous, or intraarterial administration.

The composition can be administered in or on a device that allows controlled or sustained release, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the AAV vector. The composition also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BEET), and/or a polylactic-glycolic acid.

The dose of the vector in the composition administered to the mammal will depend on a number of factors, including the size (mass) of the mammal, the extent of any side-effects, the particular route of administration, and the like. Preferably, the inventive method comprises administering a "therapeutically effective amount" of the composition comprising the inventive vector described herein. A "therapeutically effective amount" refers to an amount effective, at dosages and for periods of time necessary, to achieve a desired therapeutic result. The therapeutically effective amount may vary according to factors such as the degree of allergen sensitivity, age, sex, and weight of the individual, and the ability of the vector to elicit a desired response in the individual.

In another embodiment, the inventive method can comprise administering a "prophylactically effective amount" of the composition comprising the inventive vector. A "prophylactically effective amount" refers to an amount effective, at dosages and for periods of time necessary, to achieve a desired prophylactic result (e.g., prevention of an immune response or allergic reaction). Subjects that are in need of prophylactic administration can be readily determined by routine allergy testing known in the art. Additionally, subjects with a previous allergic reaction can be treated prophylactically against future allergic reactions.

The vector encoding the anti-IgE antibody (or a soluble IgE receptor, an eosinophil, a basophil, IL-13, or IL-4) may be administered multiple times during a therapeutic or prophylactic treatment period and/or employ multiple administration routes, e.g., intramuscular and subcutaneous, to ensure sufficient exposure of cells to the composition. For example, the composition may be administered to the mammal two or more times (e.g., 2, 3, 4, 5, 6, 6, 8, 9, or 10 or more times) during a therapeutic or prophylactic treatment period. However, according to preferred aspects of the invention, a single administration of the vector described herein (or composition comprising the vector) is sufficient to provide a prolonged expression of the anti-IgE antibody (or a soluble IgE receptor, an eosinophil, a basophil, IL-13, or IL-4) at therapeutic or prophylactic levels in the mammal, sufficient to inhibit or reduce an immune response or allergic reaction to an allergen as compared to the immune response or allergic reaction in the absence of therapy, with minimal side effects. In some embodiments, the expression level is sufficient to inhibit or reduce an immune response or allergic reaction to multiple exposures to an allergen (e.g., exposure to the allergen 2 or more times, 3 or more times, 5 or more times, or even 10 or more times) between treatments. Preferably, the therapeutic levels are expressed in the mammal, after administration of the vector or composition comprising same, for about 30 days or more (e.g., about 45 days or more, about 60 days or more, about 75 days or more, about 90 days or more, about 4 months or more, about 6 months or more, about 10 months or more, or even about 12 months or more). Thus, in some embodiments, the method comprises administering the vector to the mammal not more than once within about 30 days, not more than once within about 45 days, not more than once within about 60 days, not more than once within about 75 days, or even not more than once within about 90 days (e.g., not more than once within about 4 months, about 5 months, about 6 months, about 10 months, or about 12 months).

The dose of vector in the composition required to achieve a particular therapeutic or prophylactic effect (i.e., reduction or inhibition of an allergic reaction) typically is administered in units of vector genome copies per cell (gc/cell) or vector genome copies/per kilogram of body weight (gc/kg). One of ordinary skill in the art can readily determine an appropriate vector dose range to treat a patient having a particular immune response based on these and other factors that are well known in the art.

The present invention also provides a method of providing a recombinant humanized mouse model of allergy comprising delivering peripheral blood mononuclear cells (PBMC) from a human subject with an allergy into an immunodeficient mouse. In a preferred embodiment the blood mononuclear cells are from a human subject with any allergy with a clinical history of anaphylaxis. The allergy can be to any allergen as previously disclosed herein, preferably a food allergen, pollen, dust mite, insect venom, peanut, tree nut, or bee sting venom. In a more preferred embodiment the human subject has a peanut allergy with a clinical history of anaphylaxis. The PBMC cells can be delivered into the immunodeficient mouse by any suitable method, such as by injection (e.g., intraperitoneal or intravenous injection). The PBMCs can, optionally, be co-administered to the mouse with the relevant antigen. In a related aspect, the invention also provides a humanized immunodeficient mouse suitable for use as a model of allergy, wherein the mouse comprises PBMCs from a human subject with an allergy to an allergen, and the mouse exhibits an immune response or allergic reaction when exposed to the allergen. The PBMC's can be from a human subject with an allergy to any allergen as previously disclosed herein, such as a food allergen, pollen, dust mite, insect venom, peanut, tree nut, or bee sting venom. In a preferred embodiment the PBMCs are from a human subject with a peanut allergy and a clinical history of anaphylaxis.

The following examples further illustrate the invention but, of course, should not be construed as in any way limiting its scope.

Example 1

This example demonstrates the development of a recombinant humanized mouse model of peanut allergy.

Heparinized blood was obtained from donors with allergy to peanut or non-allergic healthy control subjects. Specific sensitization was documented by detection of allergen-specific IgE in the sera of donors (ImmunoCAP specific IgE blood test; Phadia AB, Uppsala, Sweden). Blood mononuclear cells were isolated from heparinized blood by using Ficoll-Paque density centrifugation (Ficoll® Paque Plus, Sigma Aldrich, St Louis, Mo.). The absence of detectable human IgG in mouse sera was checked by ELISA prior to reconstitution with human cells.

Cells isolated by the Ficoll-Paque method were administered to 6 to 8 week old NOD-scid IL@Rgamma$^{null}$ (NSG) mice. Each animal received intraperitoneally 3×10$^7$ blood mononuclear cells in RPMI (Sigma Aldrich, St Louis, Mo.) mixed together with 100 µg of crude peanut in a total volume of 200 µl of 0.9% Sodium Chloride, split in two separate injection sites (100 µl each).

Protein extracts from roasted unsalted peanuts (*Arachis hypogaea*; Hampton Farms; Severn, N.C.) were made on the same day of administration to mice by mixing 25 g ground peanut with 250 ml 20 mM Tris buffer, pH 7.2. After 2 hr, 23° C., the aqueous fraction was collected and subsequently centrifuged to remove residual traces of fat and insoluble particles. Protein concentrations were determined using Bradford analysis with bovine serum albumin as a standard.

Mice were sensitized at weeks 0 to 4 once weekly with 100 µg of crude peanut extract via intraperitoneal injection. Mice were then challenged, weeks 5 to 10, via intragastric gavage with 300 µg of crude peanut extract using a curved 20 gauge needle (FIG. 1A) and observed for up to 4 hr after the procedure for signs of an allergic reaction. In order to maximize absorption of peanut antigen across the gastric mucosa, all mice were fasted for 8 hr prior to peanut challenge. The mice were assessed for total human IgG (FIG. 1B), total human IgE (FIG. 1C), total mouse IgE, peanut-specific (PN-specific) human IgE (FIG. 1D), anaphylactic symptoms (FIG. 1E), anaphylaxis score (FIG. 1F), plasma histamine (FIG. 1G), and passive cutaneous anaphylaxis (FIG. 1H).

The results show that mice reconstituted with mononuclear cells of a donor with or without peanut allergy had increasing levels of human IgG following reconstitution (FIG. 1B). In contrast, after peanut sensitization, only the mice reconstituted with mononuclear cells from the peanut allergic subjects expressed total human IgE and peanut-specific IgE (FIGS. 1C and 1D). Importantly, mice reconstituted with blood mononuclear cells from a peanut allergic donor showed a clinical phenotype associated with an allergic response. Mice displayed puffiness around the eyes and snout, pilar erecti, itching/ruffling of fur, and decreased ambulation and respiratory rate (FIG. 1E) with an anaphylaxis score of 2±1 (FIG. 1F). These clinical characteristics were not observed in the animals that received blood mononuclear cells from a non-allergic individual. Histamine levels in mice reconstituted with blood mononuclear cells from a peanut allergic donor and then challenged with crude peanut extract, displayed elevated levels of histamine after peanut challenge, when compared with mice reconstituted with blood mononuclear cells from a non-peanut allergic, non-atopic donor (FIG. 1G).

Taken together, the results from these studies show that mice reconstituted with blood mononuclear cells from a peanut allergic donor showed a phenotype associated with an allergic response, whereas these characteristics were not observed in the animals that received blood mononuclear cells from a non-allergic donor.

To demonstrate that the peanut-induced anaphylaxis in the reconstituted NOD-scid IL2Rgamma$^{null}$ mice was mediated by human IgE, a subset of reconstituted mice were treated a single time with 250 µg omalizumab (Xolair®; Novartis, Huningue, France), a dose based on per weight basis as has been used in other murine studies. The mice were evaluated before therapy and 1 week after therapy for IgE and 2 weeks after therapy for physical assessment of the mice for anaphylaxis signs and passive cutaneous anaphylaxis.

The results show that mice treated with omalizumab after the first sign of anaphylactic symptoms had free IgE levels that were significantly lower ($p<0.001$) 1 week after omalizumab administration compared to the levels one week previous to the therapy (FIG. 2A). The omalizumab mice appeared normal after peanut challenge; 2 weeks post omalizumab therapy (compare FIG. 2B to FIG. 1E). Finally, omalizumab blocked peanut-induced peanut-specific IgE-mediated passive cutaneous anaphylaxis, similar to that observed with serum from a non-peanut allergic donor which induced no dye extravasation (FIG. 2C).

Taken together the results of Example 1 confirm the development of a mouse model of peanut allergy.

Example 2

This example demonstrates the design and expression of an AAV-vector comprising a promoter operably linked to a nucleic acid sequence that encodes an anti-hIgE antibody.

The expression cassette consists of the cytomegalovirus (CMV) enhancer and chicken-β-actin promoter (CAG promoter) operably linked to the anti-hIgE monoclonal heavy and light chain cDNA sequence and the rabbit β-globin polyadenylation signal. The full length heavy and light chain amino acid sequences from the humanized anti-IgE antibody SEQ ID NOs: 10 and 11 were back-translated using human preferred codons, and sequences were optimized for improved mRNA stability and protein expression. Ig Heavy and Igκ secretion signals were added to the heavy and light chains, respectively. Heavy and light chains were cloned in the same open reading frame by using a *Thosea asigna* virus (Tav) 2A cleavable sequence downstream of a furin cleavage recognition site (RKRR). Both antibody chains were expressed from the same open reading frame in an equimolar ratio (FIG. 3A).

The optimized full length anti-hIgE cDNA sequence was synthesized and cloned into the pAAV plasmid-under control of the CAG promoter. The AAVanti-hIgE vector was produced by co-transfection into human embryonic kidney 293T cells (HEK 293T; American Type Culture Collection) of the pAAV plasmid together with a plasmid carrying the AAV Rep proteins derived from AAV2 needed for vector replication, the AAVrh.10 viral structural (Cap) proteins VP1, 2 and 3, which define the serotype of the produced AAV vector; and the adenovirus helper functions of E2, E4 and VA RNA. The AAVanti-hIgE vector (referred to as "AAVrh.10anti-hIgE") was purified by iodixanol gradient and QHP anion exchange chromatography. Vector genome titers were determined by quantitative TaqMan real-time PCR analysis. A vector coding for an irrelevant antibody directed against nicotine, AAVantiNic (referred to as "AAVrh.10IgGcontrol") was used as control for the in vivo studies.

To assess AAVrh.10anti-hIgE directed expression of the monoclonal antibody in vitro, HEK 293T cells were transfected with the AAVrh.10anti-hIgE plasmid or the AAVrh.10IgGcontrol plasmid coding for an unrelated human antibody control, and supernatant was harvested 72 hr later. Anti-hIgE antibody expression in supernatant was evaluated by coomassie blue stain SDS-PAGE and Western analysis with peroxidase-conjugated goat anti-human kappa light-chain antibody and peroxidase-conjugated goat anti-human IgG antibody and enhanced chemiluminescence substrate (Bio-Rad, Hercules, Calif.). As shown in FIG. 3B, both heavy and light chains of the anti-IgE antibody were detected in cell culture supernatants.

For in vivo studies, female NOD-scid IL2Rgamma$^{null}$ (NSG) or female Balb/C mice, at 6 to 8 weeks of age the mice received a single administration of the AAVrh.10anti-hIgE vector, the AAV9anti-hIgE vector, the AAV8anti-hIgE vector, the AAVrh.10anti-nicotine vector (control), or the AAVrh.10IgGcontrol vector at $10^{11}$ genome copies (gc) by intravenous injection in 100 µl volume.

Blood (100 µl) from the tail vein was assessed at time 0 and at various time points, until 24 weeks. The blood samples were allowed to clot for 1 hr, 23° C., followed by 30 min, 4° C., and then spun at 1,800 g for 20 min to collect serum. The concentration of anti-IgE antibody was then determined by ELISA. Wells of flat bottomed 96-well EIA/RIA plates (Corning, Corning, N.Y.) were coated with 0.2 µg human IgE, in 100 µl carbonate-buffer (pH 9.6) overnight at 4° C. and then washed with 0.05% Tween 20 in PBS (PBS-Tween) and blocked with 5% dry milk in PBS for 60 min, 23° C. Serial dilutions of sera were added to wells and incubated for 60 min, 23° C. The plates were washed 3 times with PBS-Tween and 100 µl of 1:2000 diluted mouse anti-human IgG conjugated to horseradish peroxidase (Abcam, Cambridge, Mass.) in 1% dry milk in PBS, incubated for 60 min, 23° C. After 4 wash steps, peroxidase substrate (100 µl/well; Bio-Rad, Hercules, Calif.) was added to each well, incubated for 15 min at 23° C. and the reaction was stopped with addition of 2% oxalic acid (100 µl/well). Absorbance was measured at 415 nm. Anti-hIgE antibody titers were calculated by interpolation of the log (OD)-log (dilution) with a cutoff value equal to twice the absorbance of background and converted to µg/ml based on standard curve with omalizumab antibody (Genentech, San Francisco, Calif.), quantified by the Pierce™ BCA Protein Assay Kit (Life Technologies, Grand Island, N.Y.). As shown in FIG. 3C expression of human anti-IgE at levels greater than 200 µg/ml was demonstrated for the duration of the experiment (44 weeks), while no human anti-IgE was detected from control treated animals. As shown in FIGS. 3D-3E expression of human anti-IgE was demonstrated for each of the AAV anti-IgE vectors, while no human anti-IgE was detected from control treated animals.

These data demonstrate that the AAV-anti-hIgE antibody expression cassette can provide high-level, specific, long-term anti-IgE antibody expression from a single administration.

Example 3

This example demonstrates prophylactic therapy with the AAV-anti-hIgE vector to reduce an allergic reaction to an allergen To test whether pre-treatment with AAVrh.10anti-hIgE would protect peanut allergic mice, NOD-scid IL2R$\gamma^{null}$ mice (6 to 8 week old) were treated with AAVrh.10anti-hIgE ($10^{11}$) or AAVrh.10IgGcontrol ($10^{11}$) on week −3 and then reconstituted with blood mononuclear cells on week 0. The mice were subsequently challenged with peanut extract (FIG. 4A). From 2 week post-vector injection, anti-hIgE antibody levels were evaluated every 2 weeks. Mice were sensitized and challenged with crude peanut extract on weeks 0 to 4 and 5 to 8 respectively. Human IgG levels were evaluated at weeks 2, 4 and 8. Human IgE and peanut-specific IgE was evaluated at week 4. Free-IgE levels were evaluated at week 4. An anaphylaxis score was evaluated 30 min after each peanut challenge, locomotor activity was evaluated at week 6, histamine levels week 7 and passive cutaneous anaphylaxis week 7.5.

Following blood mononuclear cells transfer and sensitization with peanut extract, total human IgE, peanut specific IgE and free IgE levels were induced (FIGS. 4B-D). An IgE response developed only when the specific allergen was administered to NSG mice reconstituted with blood mononuclear cells from a peanut allergic donor. Mice treated with AAVrh.10anti-hIgE had significantly lower levels of total and peanut-specific IgE from day 28 onwards when compared with mice treated with AAVrh.10IgGcontrol (p<0.002). Importantly, free IgE levels were significantly lower in AAVrh.10anti-hIgE treated mice compared to the AAVrh.10IgG control treated mice (p<0.01; FIG. 4D). Anaphylactic responses were evaluated 30 min after intragastric challenge with peanut extract. Strikingly, AAVrh.10anti-hIgE treated mice displayed a far less severe allergic phenotype compared to those that received the control vector as defined by clinical phenotype, suppressed ambulation, a lower anaphylaxis score, decreased histamine release, and decreased PCA. (FIG. 5A-D).

These data demonstrate that a single prophylactic treatment of the AAVrh.10anti-hIgE vector can reduce or inhibit an immune response or allergic reaction.

Example 4

This example demonstrates the effectiveness of vector administration after exposure to antigen.

To determine whether treatment with antiAAVrh.10anti-hIgE could protect peanut allergic mice after the mice had been sensitized with peanut extract and exhibited peanut extract-induced allergic reactions, NOD-scid IL2Rgamma$^{null}$ mice were reconstituted with blood mononuclear cells at week 0 and then sensitized and challenged with crude peanut extract at week 0 to 4 and 5 to 10, respectively. After the first signs of anaphylaxis associated with peanut challenge (week 5), mice were administered AAVrh.10anti-hIgE, AAVrh.10IgGcontrol or 250 μg of the humanized anti-IgE mAb omalizumab in 200 μl of 0.9% NaCl. Anti-hIgE antibody levels were evaluated at fixed intervals (every 2 weeks) (FIG. 6A). Human IgG levels were evaluated at weeks 2, 4 and 8. Human IgE was evaluated on weeks 4 and 6, free-IgE levels at weeks 4 and 6, and peanut-specific IgE at week 4. Anaphylaxis score and clinical score was evaluated 30 min after each peanut challenge at week 7 and 10. Locomotor activity was evaluated at weeks 7 and 10, histamine levels at weeks 6 and 9 and passive cutaneous anaphylaxis at weeks 7 and 10.

Following blood mononuclear cells transfer and sensitization with peanut extract, an IgE response developed only when the specific allergen was injected in the group of NSG mice reconstituted with blood mononuclear cells from a peanut allergic donor and was sustained after peanut challenge (FIG. 6B). All mice developed peanut specific IgE after completing peanut sensitization at week 4, 1 week prior to therapy (FIG. 6C). Free IgE levels in the AAVrh.10anti-hIgE-treated mice were significantly reduced 1 week after therapy (week 6; p<0.01) compared to the AAVrh.10IgGcontrol treated mice (FIG. 6D). At week 10, 5 weeks after therapy with AAVrh.10anti-hIgE, the peanut allergic mice had no clinical signs, while peanut allergic mice treated with omalizumab had puffiness around the eyes and snout, pilar erecti, itching and ruffling of fur (FIG. 7A). At week 7, 2 weeks after therapy, both AAVrh.10anti-hIgE and omalizumab treated mice were significantly more ambulatory than the control (FIG. 7B, left), but at week 10, 5 weeks after therapy, the AAVrh.10anti-hIgE mice were significantly more ambulatory than the omalizumab treated mice (FIG. 7B right; by week 10, all of the control mice had died). Consistent with the clinical phenotype and ambulatory data, the anaphylaxis score at 7 week (2 weeks after therapy) was significantly lower for both the AAVrh.10anti-hIgE and omalizumab treated mice compared to the control, but at 10 week (5 weeks after therapy) only the AAVrh.10anti-hIgE therapy continued to be efficacious, with the omalizumab mice similar to the control mice at week 7 (by week 10 all of the control mice had died; FIG. 7C). The same observations were made for plasma histamine levels (FIG. 7D) and passive cutaneous anaphylaxis (FIG. 7E).

The most striking observation was analysis of survival. Over 40 days after therapy, only mice that received AAVrh.10anti-hIgE were protected against death (FIG. 8). Ninety % of AAVrh.10anti-hIgE mice (9/10) survived up to 40 days after therapy (the last time point assessed), while 70% (7/10) of omalizumab treated mice died and 89% (8/9) AAVrh.10IgGcontrol mice died. Consistent with xenographic graft-versus-host disease (GVHD) inflammatory and immune infiltrates in mice, were seen in both lung and small intestine in humanized mice 6 to 7 weeks after reconstitution with mononuclear cells from both allergic and non-allergic donors (Table I). Diagnostic features of pulmonary GVHD, namely lymphohistiocytic, plasmacytic and neutrophilic perivasculitits and peribronchiolitis, diffuse interstitial neutrophilia and multifocal bronchiolar intraepithelial eosinophilic inclusions was seen in lung tissue. Small intestine tissue showed histologic features consistent with GVHD, namely eosinophilic, neutrophilic and lymphocytic infiltrates.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of inhibiting or reducing an immune response or allergic reaction to an allergen in a mammal, comprising administering an AAV vector to the mammal,
wherein the AAV vector comprises a promoter operably linked to a nucleic acid sequence that encodes an anti-IgE antibody or antigen binding fragment thereof, and
wherein the vector is administered to the mammal not more than once within about 30 days,
whereupon the nucleic acid is expressed and an immune response or allergic reaction against the allergen is inhibited or reduced.

2. The method of claim 1, wherein, after administration of the vector, the mammal expresses therapeutic or prophylactic levels of the anti-IgE antibody or antigen binding fragment thereof for about 30 days or more.

3. The method of claim 1, wherein the vector is administered to the mammal prophylactically.

4. The method of claim 1, wherein the allergen is selected from the group consisting of a food allergen, pollen, dust mite, insect venom, bee sting venom, peanut, and tree nut.

5. The method of claim 1, wherein the method prevents the onset of anaphylaxis.

6. The method of claim 1, wherein the mammal is a human.

7. The method of claim 1, wherein the vector is administered to the mammal by a route of administration selected from the group consisting of intraoral, intramuscular, transdermal, intravenous, intraarterial, subcutaneous, intradermal, and intraperitoneal.

8. The method of claim 1, wherein the vector is a non-human adeno-associated (AAV).

9. The method of claim 8, wherein the non-human adeno-associated virus is a rhesus macaque adeno-associated virus.

10. The method of claim 9, wherein the rhesus macaque adeno-associated virus is the adeno-associated virus serotype rh. 10.

11. The method of claim 1, wherein the promoter is a constitutively active promoter, a cell-type specific promoter, or an inducible promoter.

12. The method of claim 1, wherein the promoter is a chicken beta-actin promoter.

13. The method of claim 1, wherein the vector is in a composition comprising a pharmaceutically acceptable carrier.

14. A method of inhibiting or reducing an immune response or allergic reaction to an allergen in a mammal, comprising administering an AAV vector to the mammal,
wherein the AAV vector comprises a promoter operably linked to a nucleic acid sequence that encodes an anti-IgE antibody or antigen binding fragment thereof,
wherein the anti-IgE antibody or antigen binding fragment thereof comprises a heavy chain polypeptide and a light chain polypeptide,
wherein the heavy chain polypeptide comprises three complementarity determining regions (CDRs), wherein CDR-H1 comprises the nucleic acid sequence of SEQ ID NO: 1, CDR-H2 comprises the nucleic acid sequence of SEQ ID NO: 2, and CDR-H3 comprises the nucleic acid sequence of SEQ ID NO: 3; and
wherein the light chain polypeptide comprises three CDRs, wherein CDR-L1 comprises the nucleic acid sequence of SEQ ID NO: 4, CDR-L2 comprises the nucleic acid sequence of SEQ ID NO: 5, and CDR-L3 comprises the nucleic acid sequence of SEQ ID NO: 6,
whereupon the nucleic acid is expressed and an immune response or allergic reaction against the allergen is inhibited or reduced.

15. The method of claim 14, wherein the anti-IgE antibody or antigen binding fragment thereof comprises a heavy chain variable region comprising SEQ ID NO: 7, and a light chain variable region comprising SEQ ID NO: 8.

16. The method of claim 14, wherein the vector comprises the nucleic acid sequence of SEQ ID NO: 9.

17. The method of claim 14, wherein the vector is administered to the mammal prophylactically.

18. The method of claim 14, wherein the allergen is selected from the group consisting of a food allergen, pollen, dust mite, insect venom, bee sting venom, peanut, and tree nut.

19. The method of claim 14, wherein the method prevents the onset of anaphylaxis.

20. The method of claim 14, wherein the mammal is a human.

21. The method of claim 14, wherein the vector is administered to the mammal by a route of administration selected from the group consisting of intraoral, intramuscular, transdermal, intravenous, intraarterial, subcutaneous, intradermal, and intraperitoneal.

22. The method of claim 14, wherein the vector is a non-human adeno-associated (AAV).

23. The method of claim 22, wherein the non-human adeno-associated virus is a rhesus macaque adeno-associated virus.

24. The method of claim 23, wherein the rhesus macaque adeno-associated virus is the adeno-associated virus serotype rh.10.

25. The method of claim 14, wherein the promoter is a constitutively active promoter, a cell-type specific promoter, or an inducible promoter.

26. The method of claim 14, wherein the promoter is a chicken beta-actin promoter.

27. The method of claim 14, wherein the vector is in a composition comprising a pharmaceutically acceptable carrier.

* * * * *